US012054762B2

(12) United States Patent
Gomes et al.

(10) Patent No.: US 12,054,762 B2
(45) Date of Patent: *Aug. 6, 2024

(54) METHODS OF PROTEIN PRODUCTION USING ANTI-SENESCENCE COMPOUNDS

(75) Inventors: Jose Manuel Gomes, Chelmsford, MA (US); Yen-Tung Luan, Chelmsford, MA (US); Gregory Walter Hiller, Wakefield, MA (US); Wenge Wang, North Chelmsford, MA (US)

(73) Assignee: WYETH LLC, Madison, NJ (US)

( * ) Notice: Subject to any disclaimer, the term of this patent is extended or adjusted under 35 U.S.C. 154(b) by 247 days.

This patent is subject to a terminal disclaimer.

(21) Appl. No.: 12/107,533

(22) Filed: Apr. 22, 2008

(65) Prior Publication Data

US 2008/0274507 A1   Nov. 6, 2008

Related U.S. Application Data

(60) Provisional application No. 60/913,382, filed on Apr. 23, 2007.

(51) Int. Cl.
| C12N 15/19 | (2006.01) |
| C07K 14/435 | (2006.01) |
| C07K 14/705 | (2006.01) |
| C12P 21/00 | (2006.01) |
| C12P 21/02 | (2006.01) |

(52) U.S. Cl.
CPC ........ C12P 21/02 (2013.01); C07K 14/70578 (2013.01); C12P 21/005 (2013.01); C12N 2500/33 (2013.01); C12N 2510/02 (2013.01)

(58) Field of Classification Search
None
See application file for complete search history.

(56) References Cited

U.S. PATENT DOCUMENTS

| 4,816,397 A | 3/1989 | Boss et al. |
| 4,816,567 A | 3/1989 | Cabilly et al. |
| 5,223,409 A | 6/1993 | Ladner et al. |
| 5,225,539 A | 7/1993 | Winter |
| 5,585,089 A | 12/1996 | Queen et al. |
| 5,610,279 A | 3/1997 | Brockhaus et al. |
| 5,693,761 A | 12/1997 | Queen et al. |
| 5,693,762 A | 12/1997 | Queen et al. |
| 5,721,121 A * | 2/1998 | Etcheverry .......... C07K 14/525 435/325 |
| 5,808,029 A | 9/1998 | Brockhaus et al. |
| 5,830,761 A | 11/1998 | Drapeau et al. |
| 5,859,205 A | 1/1999 | Adair et al. |
| 6,146,847 A | 11/2000 | Goffe et al. |
| 6,300,064 B1 | 10/2001 | Knappik et al. |
| 6,407,213 B1 | 6/2002 | Carter et al. |
| 2003/0040095 A1 | 2/2003 | Arini et al. |
| 2003/0070185 A1 | 4/2003 | Jakobovits et al. |
| 2004/0014814 A1* | 1/2004 | Grigg et al. ................. 514/563 |
| 2006/0069513 A1 | 3/2006 | Playford |
| 2006/0121568 A1 | 6/2006 | Drapeau et al. |
| 2006/0121569 A1 | 6/2006 | Drapeau et al. |
| 2006/0160180 A1 | 7/2006 | Drapeau et al. |
| 2007/0110743 A1 | 5/2007 | Drapeau et al. |
| 2008/0081356 A1 | 4/2008 | Lasko et al. |

FOREIGN PATENT DOCUMENTS

| EP | 0171496 | 3/1985 |
| EP | 0173494 | 3/1986 |
| EP | 0239400 | 9/1987 |
| EP | 4178014 | 3/1991 |
| GB | 2177096 | 9/1985 |
| WO | WO9002809 | 3/1990 |
| WO | WO9209690 | 3/1991 |
| WO | WO9117271 | 11/1991 |
| WO | WO9201047 | 4/1992 |
| WO | WO-92/09298 | 6/1992 |
| WO | WO9206193 | 6/1992 |
| WO | WO-9209298 | 6/1992 |
| WO | WO9218619 | 9/1992 |
| WO | WO9215679 | 10/1992 |
| WO | WO9220791 | 11/1992 |
| WO | WO9301288 | 1/1993 |
| WO | 95/18858 | 7/1995 |
| WO | 9518858 | 7/1995 |
| WO | WO9634096 | 10/1996 |
| WO | WO-96033735 | 10/1996 |
| WO | WO9852976 | 11/1998 |
| WO | WO 99/35242 | 7/1999 |

(Continued)

OTHER PUBLICATIONS

Mikuls et al., Expert Opinion on Pharmacotherapy, 2001, 1: 75-84.*
Yung, Curr Opin Invest Drugs, 2001, 2: 216-221, Abstract.*
Ikeda et al., Cell Structure and Function, 1999, 24: 79-8.*
Fox et al., Biotechnol Appl Biochem, 2005, 41: 255-264.*
Boldyrev et al., Neuroscience Letters, 1999, 263: 169-172.*
Hipkiss et al., Cell. Mol. Life Sci., 2000, 57: 747-753.*
Chaplen, Proc. Natl. Acad. Sci. USA, 1998, 95: 5533-5538.*
Foiles, Expert Opin. Invest. Drugs, 2001, 10: 1977-1987.*
Chaplen, Cytotechnology, 1998, 26: 173-183.*
Vlassara, Molecular Medicine, 1995, 1: 634-646.*
Yang, Biotechnol. Bioeng., 2000, 68: 370-380.*
Hipkiss, Perspect. Hum. Biol., 1995, 1: 59-70.*
Freshney, Basic Principles of Cell Culture, 2006, Chapter I, pp. 1-22.*

(Continued)

Primary Examiner — Ileana Popa
(74) Attorney, Agent, or Firm — HALEY GUILIANO LLP; Brian M. Gummow

(57) ABSTRACT

Methods of producing a protein in cell culture comprising an anti-senescence compound, such as the antioxidant carnosine, are provided. According to teachings of the present invention, cells grown in a cell culture medium comprising an anti-senescence compound exhibit increased viability and productivity. Furthermore, cell cultures grown in the presence of an anti-senescence compound exhibit decreased levels of high molecular weight aggregates in the cell culture medium.

30 Claims, 11 Drawing Sheets

(56) References Cited

FOREIGN PATENT DOCUMENTS

| | | |
|---|---|---|
| WO | 9964578 | 12/1999 |
| WO | WO-0034317 | 6/2000 |
| WO | WO-0066791 | 11/2000 |
| WO | 0138548 | 5/2001 |
| WO | WO-04037861 | 5/2004 |
| WO | 2004/058800 | 7/2004 |
| WO | 2005021578 | 3/2005 |
| WO | 2005044856 | 5/2005 |
| WO | WO-2005064013 | 7/2005 |
| WO | 2006/019447 | 2/2006 |
| WO | WO-2006/026447 | 3/2006 |
| WO | WO 2006/026447 | 3/2006 |
| WO | WO 2007/011595 | 1/2007 |
| WO | WO-2007/050498 | 5/2007 |

OTHER PUBLICATIONS

Hipkiss, "Pluripotent Protective Effects of Carnosine a Naturally Occurring Dipetide", Annals of the New York Academy of Sciences, 854:37-53, 1998.

Yim et al., "Construction and Production of Concatameric Human TNF Receptor-Immunoglobulin Fusion Protein", Journal of Microbiology and Biotechnology 14(1): 81-89, 2004.

Gille, et al, "Effect of antioxidants on hyperoxia-induced chromosmal breakage in Chinese hamster ovary cells: protection by carnosine" Mutagenesis, vol. 6, Issue 4, Jul. 1, 1991, pp. 313-318.

International Search Report, PCT/US2008/061125, date of mailing Jul. 11, 2008.

Written Opinion of the International Searching Authority, PCT/US2008/061125, date of mailing Jul. 11, 2008.

Yim Su-Bin et al., "Construction and Production of Concatameric Human TNF Receptor-Immunoglobulin Fusion Proteins," *J. Microbiol. Biotechnol.* 14(1):81-89 (2004).

Hipkiss et al., "Pluripotent protective effects of carnosine, a naturally occurring dipeptide," *Ann. NY Acad. Sci.* 854:37-53 (1998).

www.invitrogen.com/site/US/en/home/Products-and-Services/Applications/Cell-Culture/Mammalian-CellCulture.html, 2009.

Naismith and Sprang, "Tumor Necrosis Factor Receptor Superfamily", Journal of Inflammation, 47(1-2):1-7, 1996.

Bauer, "Carnosine and Homocarnosine, the Forgotten, Enigmatic Peptides of the Brain", Neurochem Res., 30(10):1339-45, Oct. 2005.

Calabrese et al., "Protective Effect of Carnosine During Nitrosative Stress in Astroglial Cell Cultures", Neurochem Res., 30(6-7):797-807, Jun.-Jul. 2005.

en.wikipedia.org/wiki/Carnosine. 2009.

Merck Index 13th. Merck & Co. NJ. USA. No. 1863 (Carnosine) 2001.

Sinacore et al., "Adaptation of Mammalian Cells to Growth in Serum-Free Media", Molecular Biotechnology, 15: 249-257, 2000.

Kipriyanov et al., "Generation of Recombinant Antibodies", Molecular Biotechnology, 12: 173-201, 1999.

Bird et al., "Single-chain antigen-binding proteins", Science, 242: 423-26, 1988.

Capel et al., "Heterogeneity of Human IgG Fc Receptors", Immunomethods, 4: 25-34. 1994.

Chothia et el., "Structural Repertoire of the Human Vh Segments", J Mol. Biol, 227: 799-817, 1992.

Cook at al., "The Human Immunoglobulin Vh Repertoire", Immunol. Today. 16(5): 237-42, 1995.

Datta et al., "Ionizing radiation activates transcription of the EGR1 gene via CArG elements", Proc. Natl. Acad. Sci. USA 89: 10149-53, 1992.

De Haas et al., "Fc receptors of phagocytes", J. Lab. Clin. Med., 126: 330-41, 1995.

Graham et al., "Characteristics of a Human Cell Line Transformed by DNA from Human Adenovirus Type 5", J Gen. Virol., 36: 59-72, 1977.

Green et al., "Antigen specific human monoclonal antibodies from mice engineered with human Ig heavy and light chains of YACs", Nature Genetics, 7: 13-21, 1994.

Hipkiss et al., "Non-enzymatic glycosylation of the dipeptide I-carnosine, a potential anti-protein-cross-linking agent", FEBS Lett., 371: 81-5, 1995.

Holliday et al., "A role for carnosine in cellular maintenance", Biochemistry (Moscow), 65: 843-848, 2000.

Huston et al., Protein engineering of antibody binding sites, Proc. Natl. Acad. Sci. USA, 85: 5879-83, 1988.

Kim et al., "Overexpression of bcl2 Inhibits Sodium Butyrate-induced Apoptosis in Chinese Hamster Ovary Cells Resulting in Enhanced Humanized Antibody Production", Biotechnol. Bioeng., 71: 184-193, 2000.

Kohen et al., "Antioxidant activity of carnosine, homocarnosine, and anserine present in muscle and brain", Proc. Natl. Acad. Sci. USA 85: 3175-79, 1988.

Kostelny et al., "Formation of a bispecific antibody by the use of leucine zippers", J. Immunol., 148:1547-53, 1992.

Kozbor et al., "The production of monoclonal antibodies from human lymphocytes", Immunology Today, 4: 72-79, 1983.

Mader et al. "A steroid inducible promoter for the controlled overexpression of cloned genes in eukaryotic cells", Proc. Natl.. Acad. Sci. USA, 90: 5603-7, 1993.

Mather et al., "Culture of Testicular Cells in Hormone-Supplemented Serum-Free medium", Annals N.Y. Acad. Sci., 383: 44-68, 1982.

Mather, "Establishment and Characterization of Two Distinct Mouse Testicular Epithelial Cell Lines", Biol. Reprod., 23: 243-51, 1980.

Manome et al., "Coinduction of c-jun gene expression and Internucleosomal DNA Fragmentation by Ionizing Radiation", Biochemistry, 32:10607-13, 1993.

McFarland et al. "Further evidence for the rejuvenating effects of the dipeptide L-carnosine on cultured human diploid fibroblasts", Exp. Gerontol., 34: 35-45, 1999.

McFarland et al., "Retardation of the senescence of cultured human diploid fibroblasts by carnosine", Exp. Cell Res., 212: 167-75, 1994.

Morrison, "Transfectomas Provide Novel Chimeric Antibodies", Science, 229: 1202-7. 1985.

Morrison et al, "Chimeric human antibody molecules", Proc. Natl. Acad, Sci, USA, 81: 6851-6855, 1985.

Oi et al., "Chimeric Antibodies", BioTechniques, 4: 214-221, 1986.

Olsson et al., "Human-human monoclonal antibody producing hybridomas: Technical Aspects", Meth. Enzymol, 92: 3-16, 1982.

Ravetch and Kinet, "Fc Receptors", Annu. Rev, Immunol., 9: 457-92, 1991.

Shao et al., "L-Carnosine reduces telomere damage and shortening rate in cultured normal fibroblasts", Biochemistry and Biophysical Research Communications, 324: 931-6, 2004.

Smith, "Heterogeneity of Human IgG Fc Receptors", Science, 228: 1315-17, 1985.

Songsivilai and Lachmann, "Bispecific antibody: a tool for diagnosis and treatment of disease", Clin. Exp. Immunol, 79: 315-21, 1990.

Spencer et al., "Controlling Signal Transduction with Synthetic Ligands", Science, 262: 1019-24, 1993.

Takeda et al., "Construction of chimeric processed immunoglobulin genes containing mouse variable and human constant region sequences", Nature, 314: 452-454, 1985.

Teng et al., "Construction and testing of mouse-human heteromyelomas for human monoclonal antibody production", Proc. Natl. Acad. Sci. USA, 80: 7308-12, 1983.

Tomlinson et al., "The Structural Repertoire of the Human Vk Domain", EMBO J., 14: 4628-38, 1995.

Tomlinson et al., "The Repertoire of Human Germline Vh Sequences Reveals about Fifty Groups of Vh Segments with different Hypervariable loops". J. Mol. Biol., 227: 776-98, 1992.

Urlaub et al., "Isolation of Chinese Hamster cell mutants deficient in dihydrofolate reductase activity", Proc. Natl. Acad. Sci. USA, 77: 4216-4220, 1980.

Zhao-Lie Chen et al., "Temperature Shift as a Process Optimization Step for the Production of Pro-urokinase by a Recombinant Chinese Hamster Ovary Cell Line in High-Density Perfusion Culture," Journal of Bioscience and Bioengineering, 97(4):239-243 (2004).

(56) References Cited

OTHER PUBLICATIONS

Lidia Ivanova "Hybrid Sindbis/Epstein-Barr Virus Episomal Expression Vector for Inducible Production of Proteins," Biotechniques, 39:209-212 (2005).

El-Rashdy M. Redwan et al., "Recombinant Human J-Chain: Fix the Protein Aggregations and Yield Maximize," Human Antibodies, 15:95-102 (2006).

Simone M. Schatz et al., "Higher Expression of Fab Antibody Fragments in a CHU Cell Line at Reduced Temperature," Biotechnology and Bioengineering, 80(4):433-438 (2003).

Alison Wedekind et al., "Optimization of the Human Adenosine A2a Receptor Yields in Saccharomyces Cerevisiae," Biotechnol. Prog. 22:1249-1255 (2006).

\* cited by examiner

Figure 1a. Effect of Carnosine on Acidic Peaks for MYO-29.
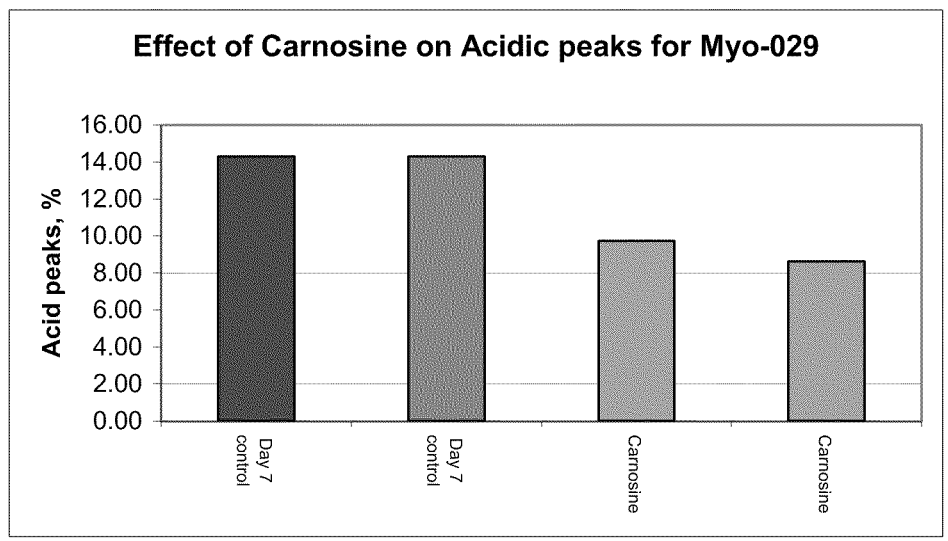
Figure 1b. Effect of Carnosine on High Molecular Weight Aggregates.
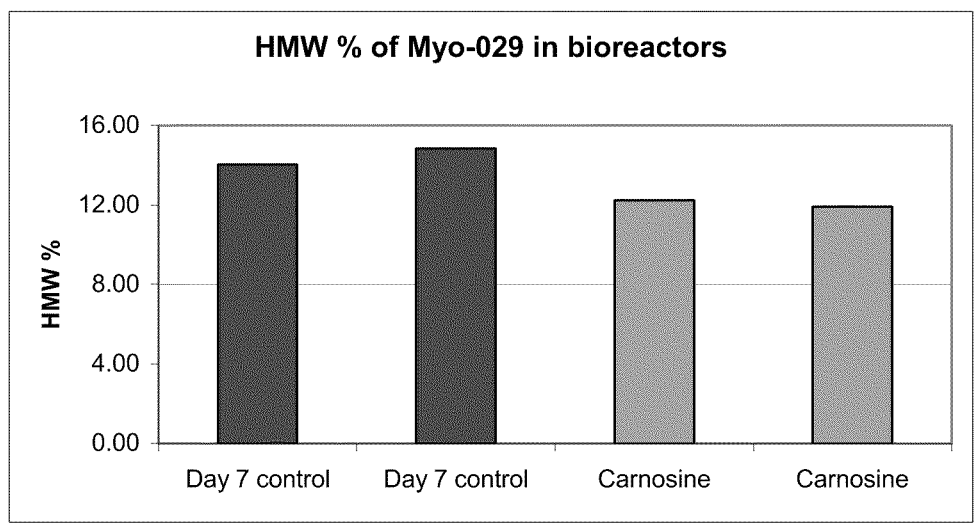

Figure 1c. Effect of Carnosine Additions on Different Days on Acidic Peaks.
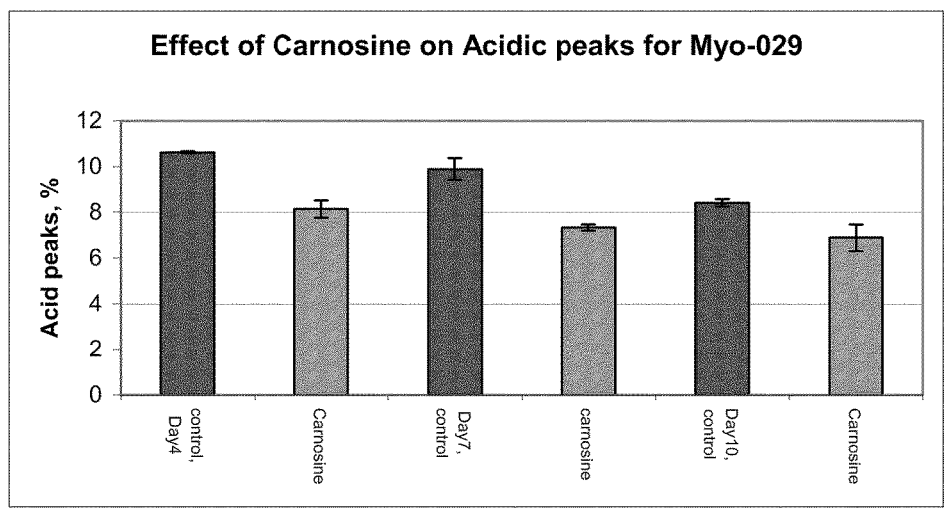
Figure 1d. Effect of Carnosine Additions on Different Days on High Molecular Weight Aggregates.
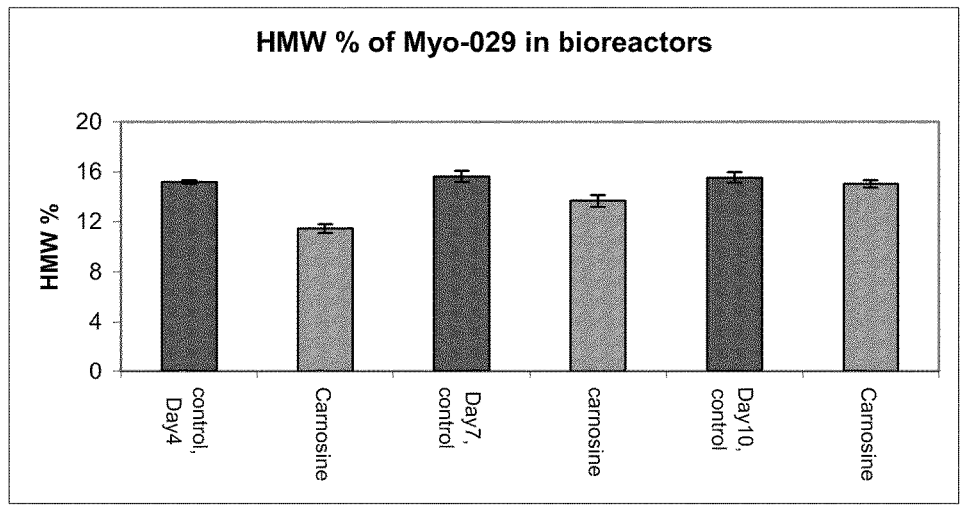

Figure 2a. Effect of Carnosine on Daily Viable Cell Density.
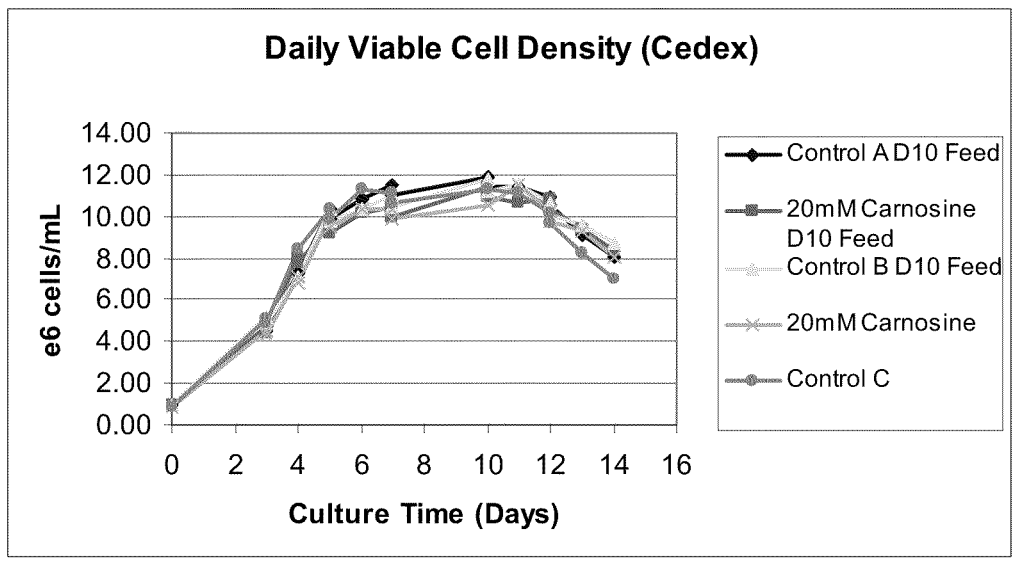
Figure 2b. Effect of Carnosine on Daily Cell Viability.
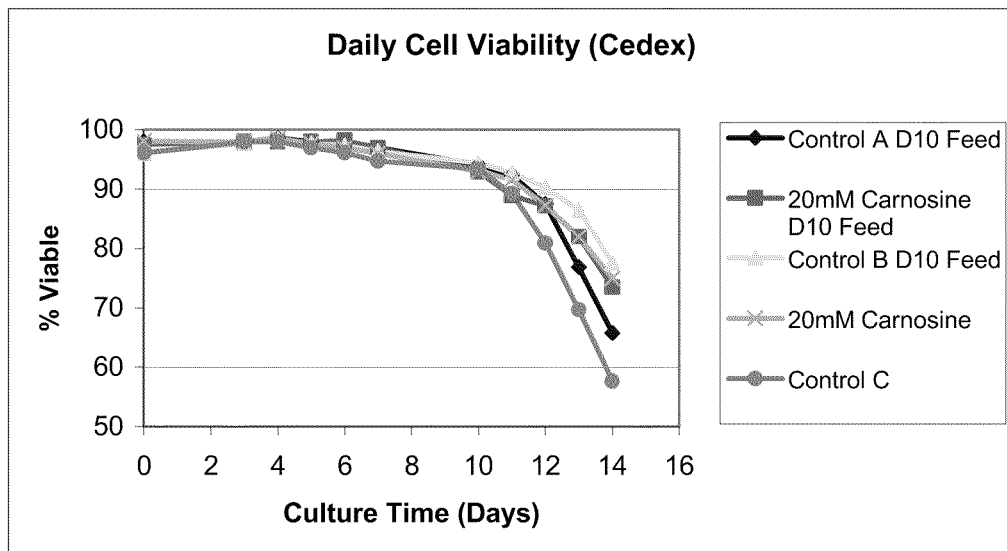

Figure 2c. Effect of Carnosine on Daily Titer.
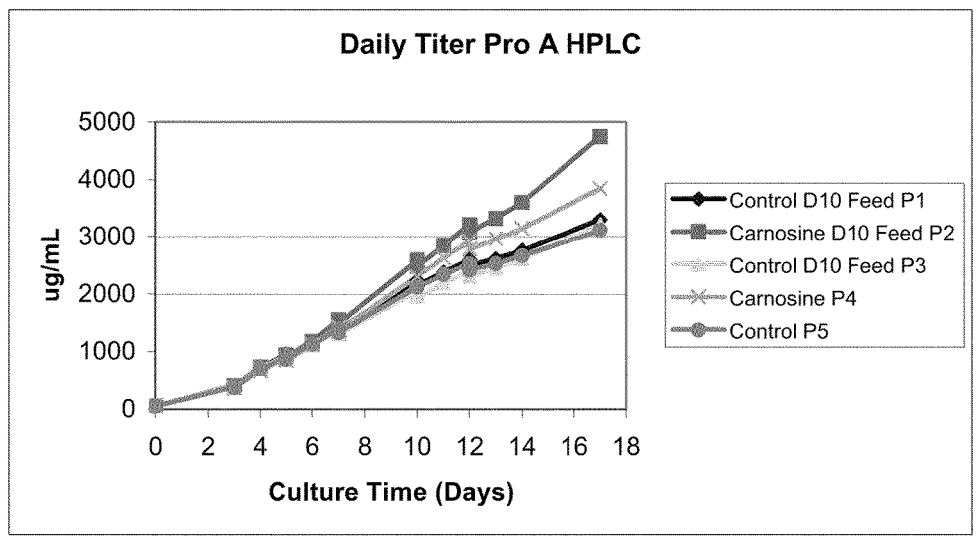
Figure 2d. Effect of Carnosine on Cumulative Specific Cellular Productivity.
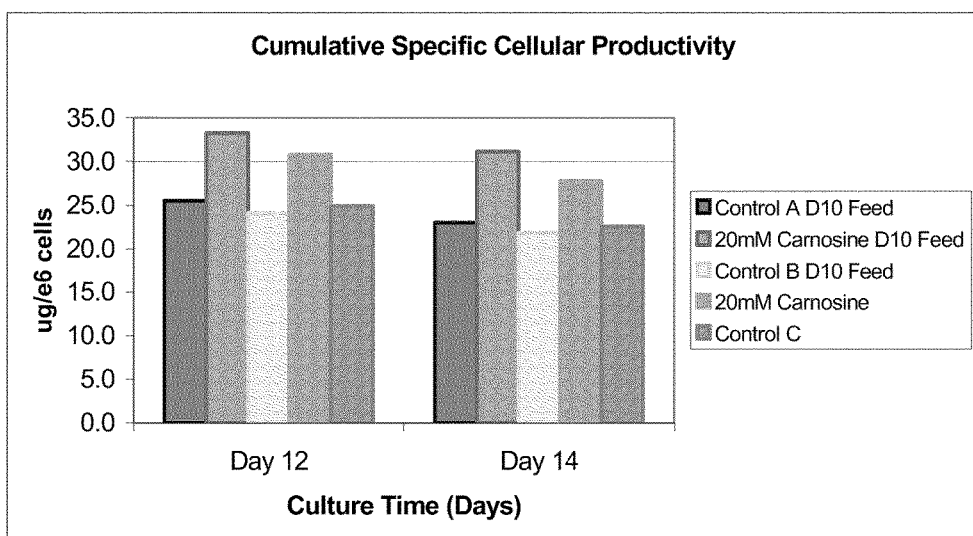

Figure 2e. Effect of Carnosine on High Molecular Weight Aggregates.
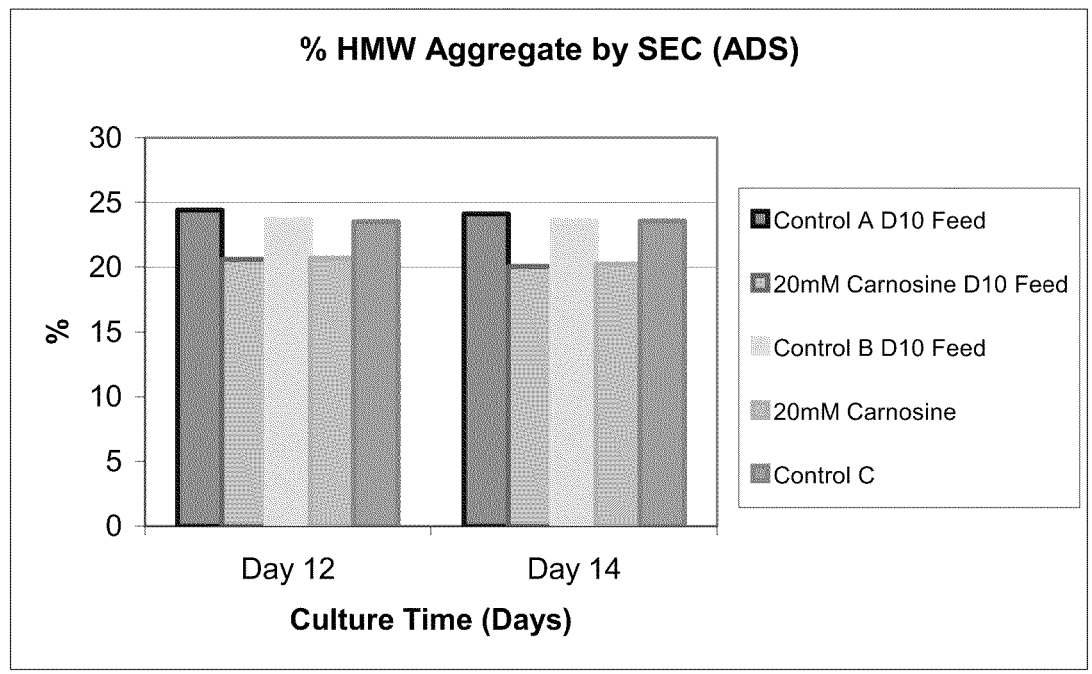
Figure 3a. Effect of Different Concentrations of Carnosine on Viable Cell Density.
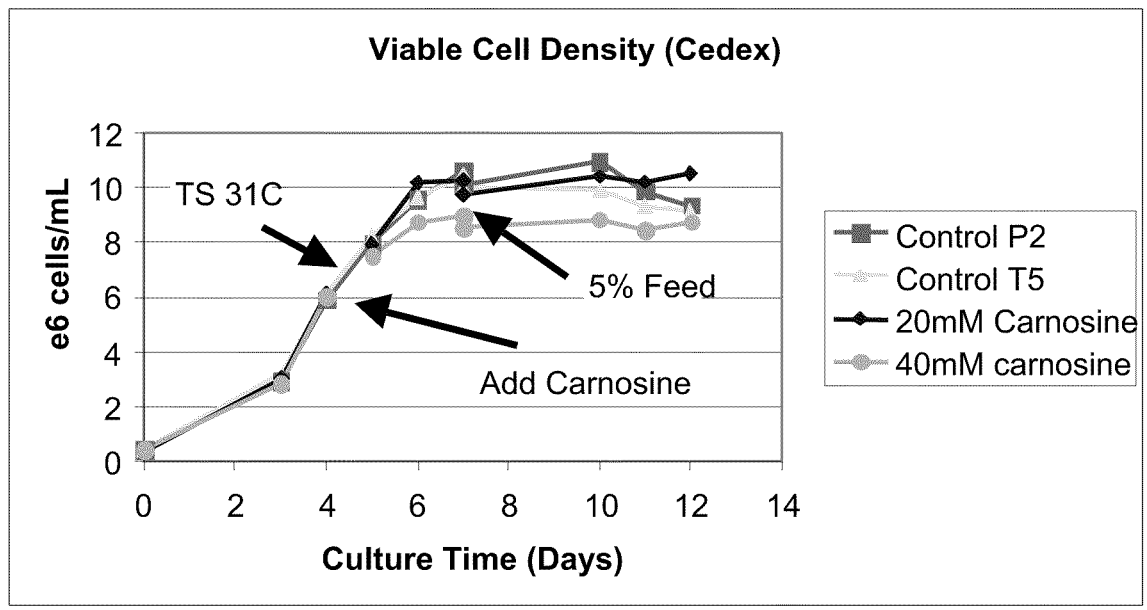

Figure 3b. Effect of Different Concentrations of Carnosine on Daily Cell Viability.
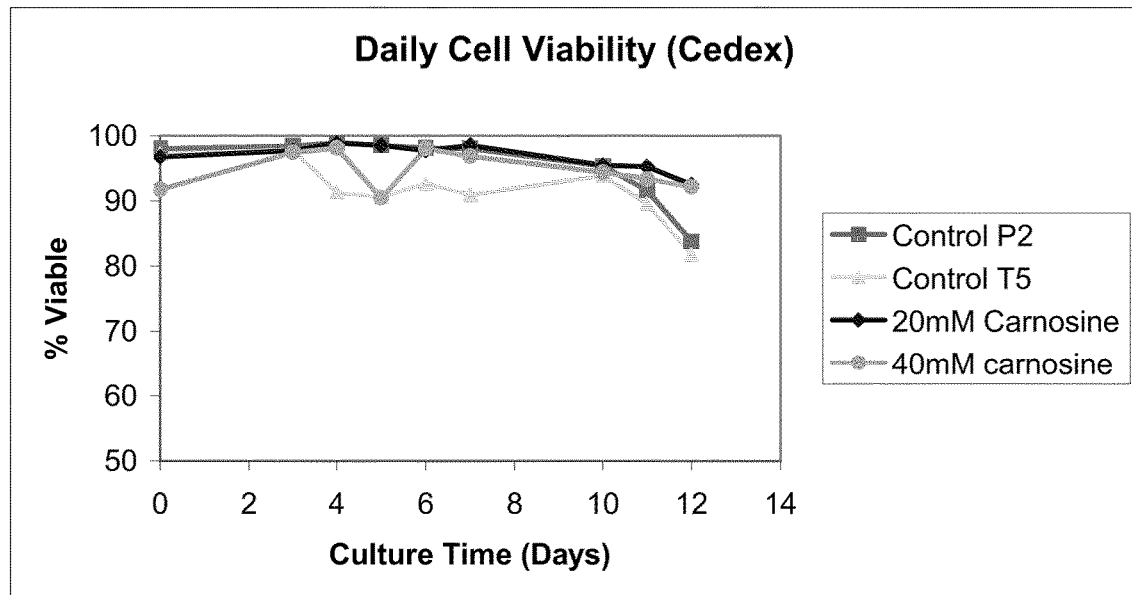
Figure 3c. Effect of Different Concentrations of Carnosine on Daily Titer.
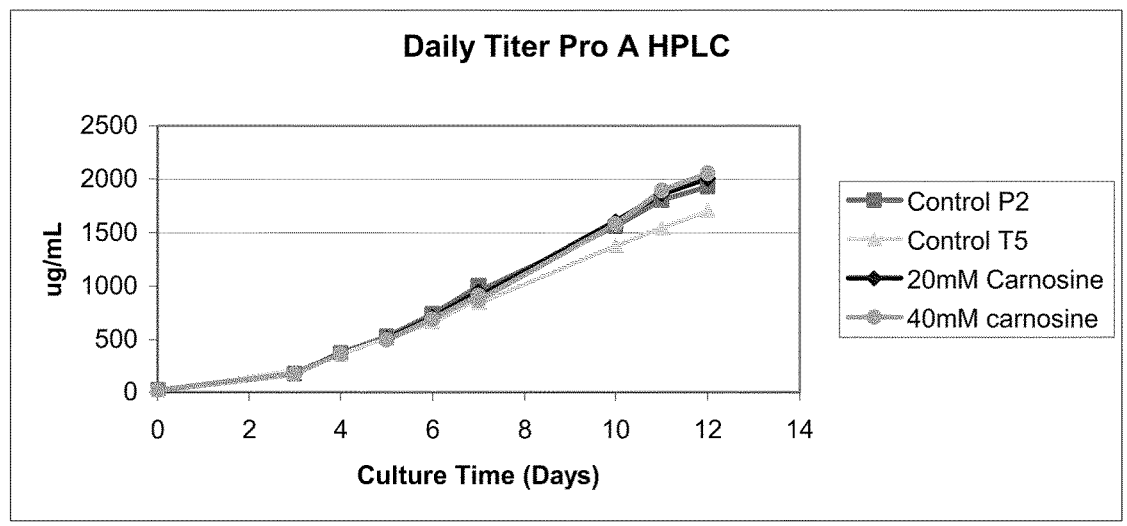

Figure 3d. Effect of Different Concentrations of Carnosine on Cumulative Specific Cellular Productivity.
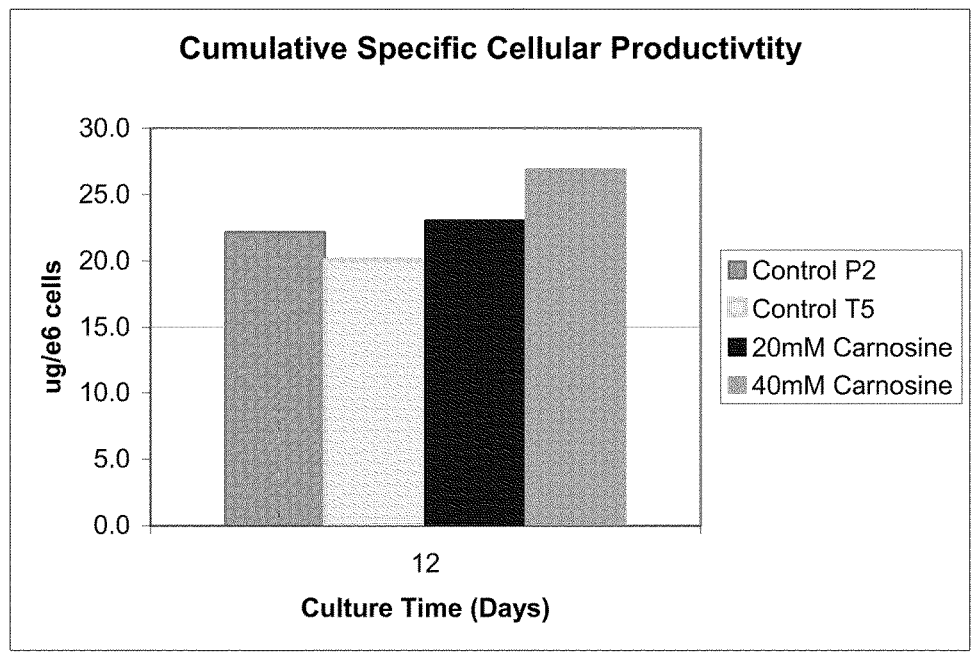
Figure 3e. Effect of Different Concentrations of Carnosine on High Molecular Weight Aggregates.
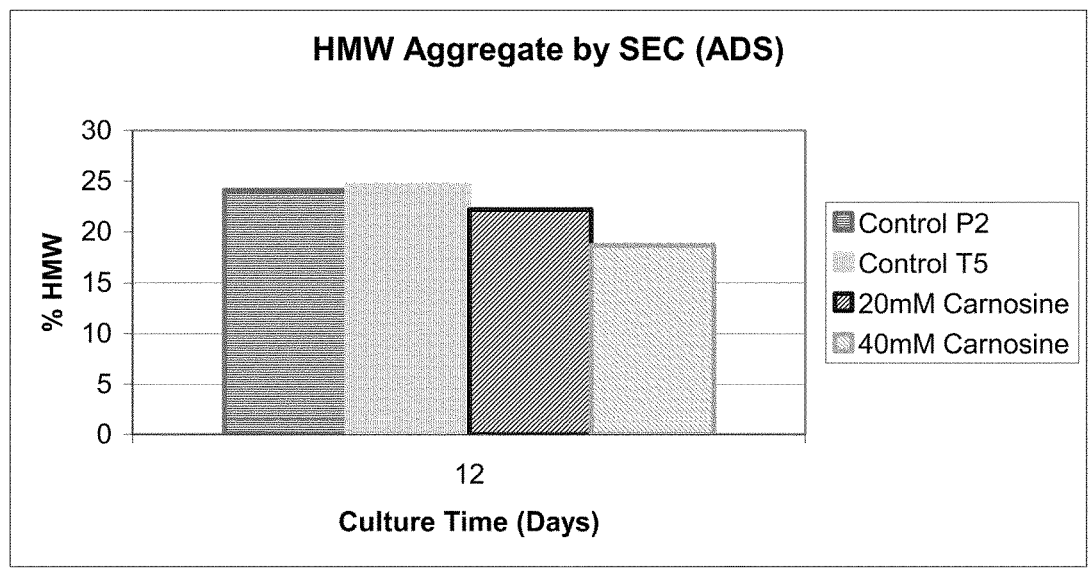

Figure 4. Viable Cell Density Profiles of a Chinese Hamster Ovary (CHO) Cell Line Producing Recombinant TNFR Fusion Protein Grown in Media Containing or Lacking Carnosine.
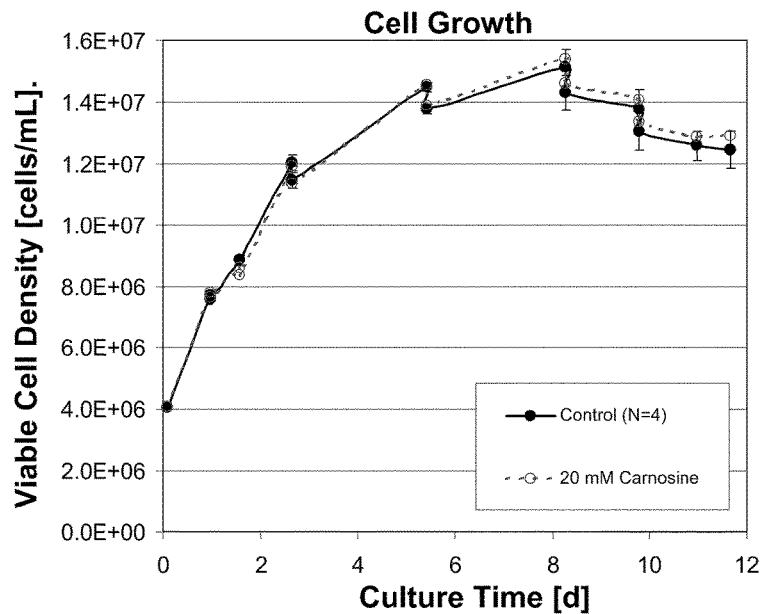
Figure 5. Cell Viability Profiles of a Chinese Hamster Ovary (CHO) Cell Line Producing Recombinant TNFR Fusion Protein in Media Containing or Lacking Carnosine.
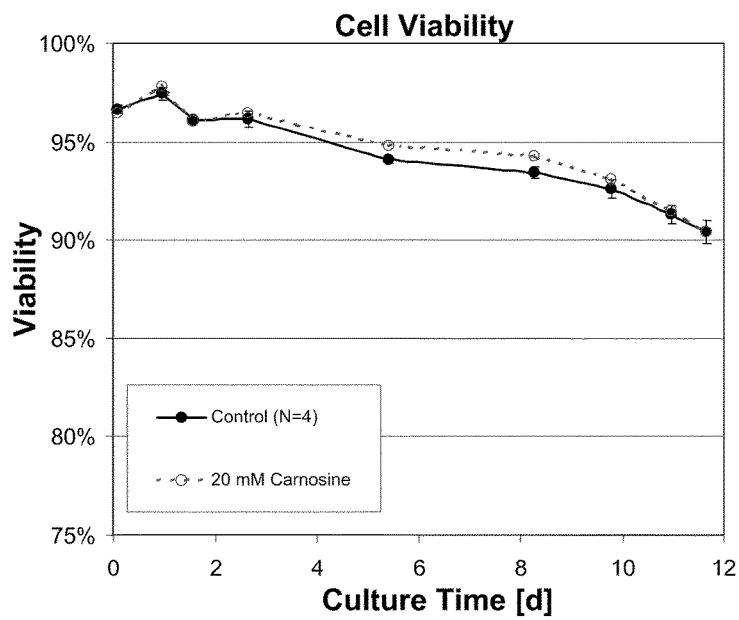

Figure 6. Effect of Carnosine on the Percentage of Aggregated/Misfolded TNFR Fusion Protein.
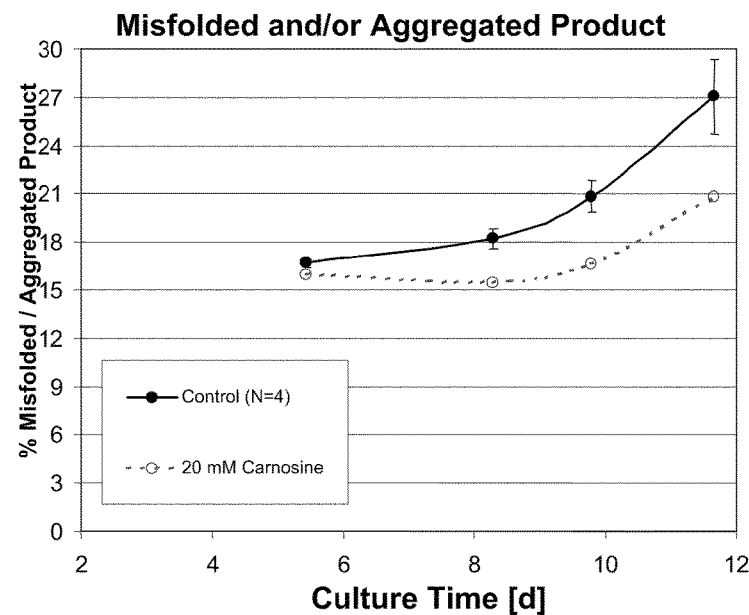
Figure 7. Effect of Carnosine on the Percentage of High Molecular Weight (HMW) Aggregates Produced by a Chinese Hamster Ovary (CHO) Cell Line Producing Recombinant TNFR Fusion Protein.
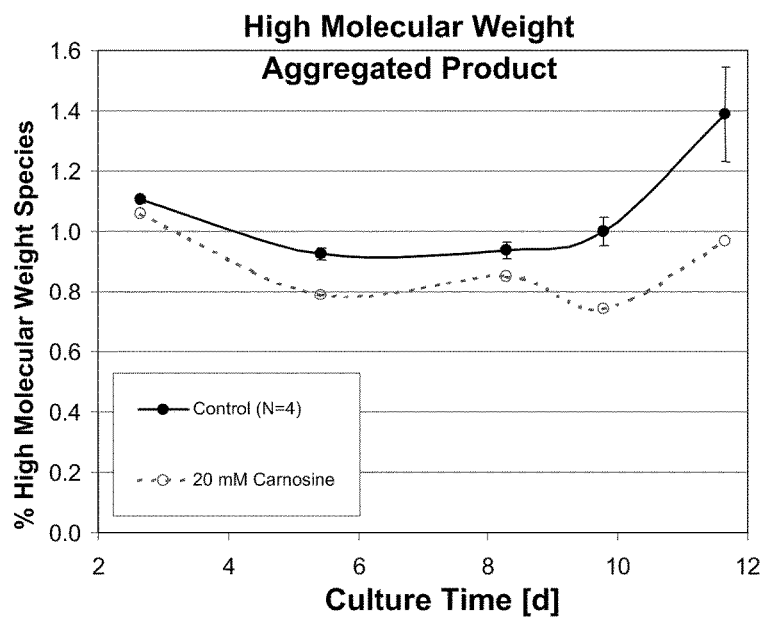

Figure 8. Product Titer Profiles of a Chinese Hamster Ovary (CHO) Cell Line Producing Recombinant TNFR Fusion Protein Grown in Media Containing or Lacking Carnosine.
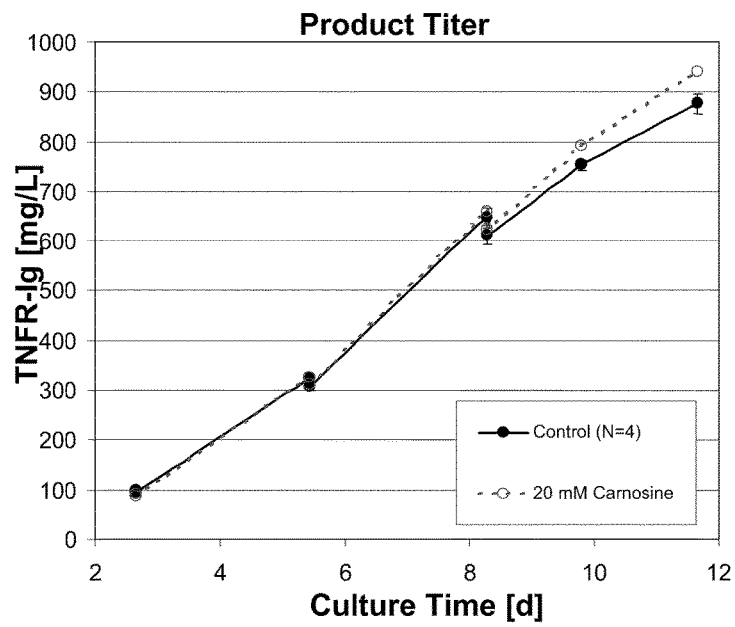
Figure 9. Specific Cellular Productivity Profiles of a Chinese Hamster Ovary (CHO) Cell Line Producing Recombinant TNFR Fusion Protein Grown in Media Containing or Lacking Carnosine.
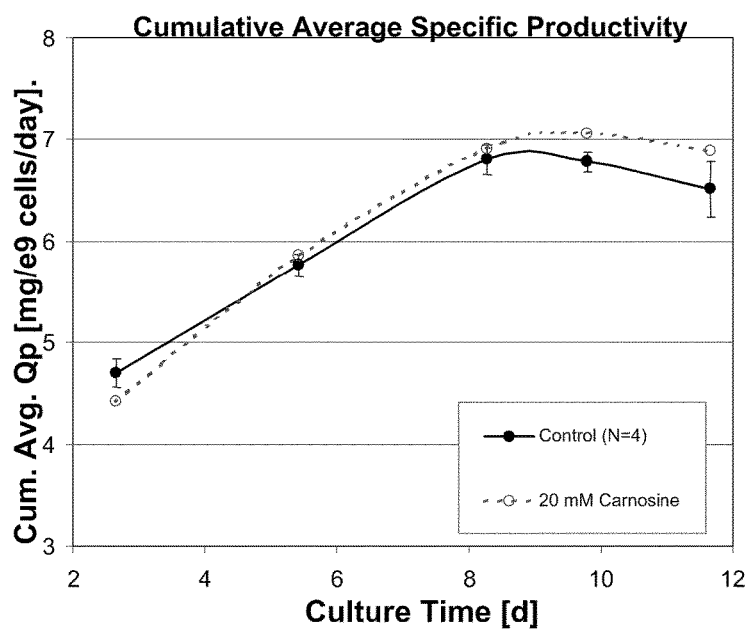

Figure 10. Total Sialylation Profiles, Expressed as a Percentage of the Reference Material, of Recombinant TNFR Fusion Protein Produced by a Chinese Hamster Ovary (CHO) Cell Line Grown in Media Containing or Lacking Carnosine.

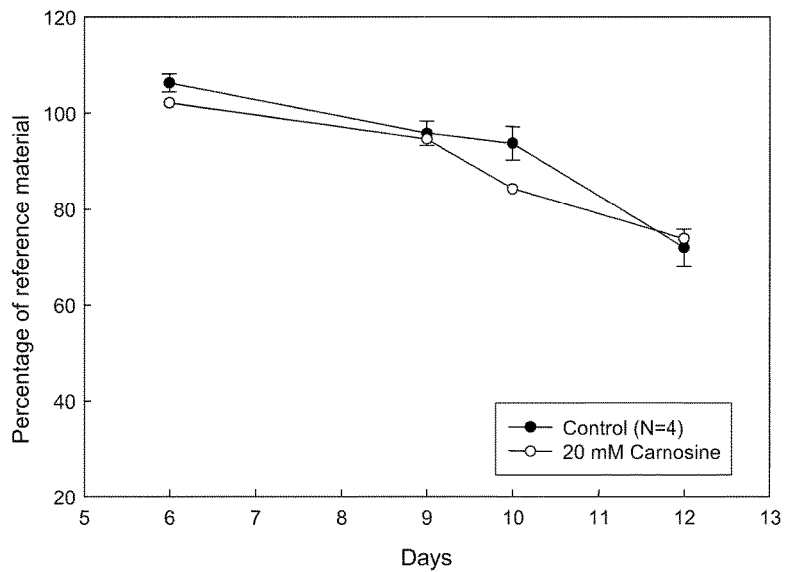

Figure 11. Distribution of Sialylated N-linked Oligiosaccharides, Expressed as a Percentage of Total N-Linked Oligosaccharides, of Recombinant TNFR Fusion Protein Produced by a Chinese Hamster Ovary (CHO) Cell Line Grown in Media Containing or Lacking Carnosine.

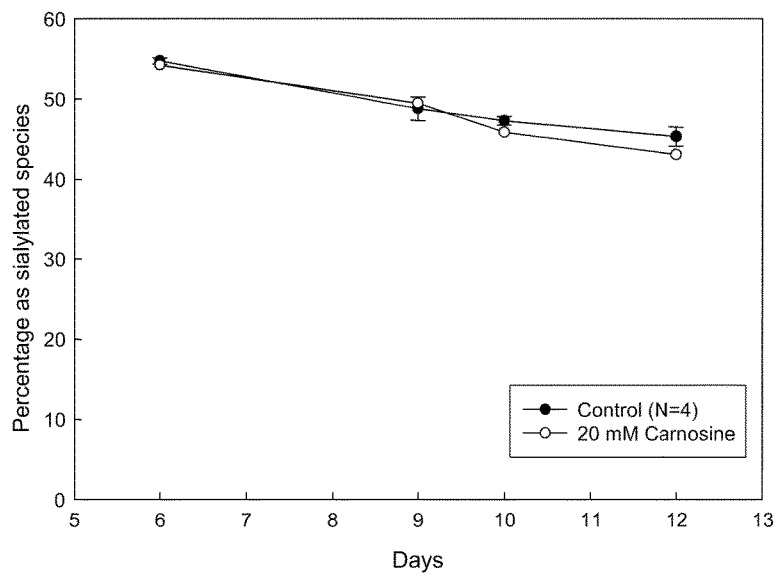

METHODS OF PROTEIN PRODUCTION USING ANTI-SENESCENCE COMPOUNDS

CROSS REFERENCE TO RELATED APPLICATIONS

This application is copending with, shares at least one common inventor with, and claims priority to U.S. provisional patent application No. 60/913,382, filed Apr. 23, 2007, the contents of which are hereby incorporated by reference in their entirety.

BACKGROUND OF INVENTION

This disclosure relates generally to the production of proteins in mammalian cell cultures. Particularly this disclosure relates to culturing mammalian cells in the presence of an anti-senescence compound, e.g. carnosine, to maintain viability and increase productivity with superior quality. Culturing cells has produced many protein products. These products, such as hybridoma-produced monoclonal antibodies, can be used for therapeutic, research or other applications. Animal cells, notably mammalian cells, are often used to produce proteins. Unfortunately, using animal cells causes the production process to be time consuming and costly.

Adding a chemical agent to a cell culture medium can increase cell productivity by inducing cells to produce a product, thereby increasing overall yield. The optimal agent to use varies depending on a number of factors, including the desired protein product and cell type. Similar factors also affect the amount of the chosen agent added and when the agent is added to the cell culture medium. Examples of agents are alkanoic acids or salts, urea derivatives, or dimethylsulphoxide (DMSO). Chemical agents, such as sodium butyrate, can have diverse effects on protein production. The addition of an agent can increase the specific productivity of the cells, but also have cytotoxic effects and can inhibit cell growth and viability.

As cells produce a protein, typically, the protein is secreted into the cell culture medium. The specific protein, however, is not the only matter in the medium; high molecular weight aggregates, acidic species, and other materials are also often in the medium, which can make the process of purification more laborious and costly. Techniques and methods are available to improve product quality, enabling more efficient protein purification; including, among others, altering the conditions of the bioreactor or using a different cell line. However, there nevertheless remains a need in the field for protein production techniques and methods that lead to improved purification processes.

Therefore, what is needed is a chemical agent that is added to the cell culture medium that can enhance the expression of a protein of interest while maintaining high cell viability. What is further needed is an agent that increases the product quality of the protein by decreasing the amount of high molecular weight aggregates and acidic species in the cell culture medium.

SUMMARY OF THE INVENTION

In certain embodiments, the present disclosure relates to a process for enhanced production of a protein product. For example, in certain embodiments, the present invention provides methods of culturing host cells expressing a protein of interest in a medium comprising an anti-senescence compound such that overall production of the protein of interest is enhanced. In certain embodiments, such an anti-senescence compound comprises carnosine.

In certain embodiments, the present invention provides compositions that enhance production of a protein of interest. Any of a variety of proteins may be produced in accordance with the methods and compositions of the present invention. For example, in certain embodiments, methods and compositions of the present invention are used to produce an antibody. In certain embodiments, methods and compositions of the present invention are used to produce a receptor, optionally linked to one or more additional protein moieties. For example, methods and compositions of the present invention may be used to produce a TNFR fusion protein.

In certain embodiments, the present invention provides a cell culture medium comprising an anti-senescence compound that enhances production of a protein of interest expressed in a host cell. In certain embodiments, such an anti-senescence compound comprises carnosine. In certain embodiments, genetically manipulated host cells are combined with an inoculum medium to form a cell culture medium, which is grown in a bioreactor. During a production run of the desired protein product, conditions of the bioreactor may be altered and/or supplements may be added in order to increase the productivity and/or maintain viability. Supplements may include a feed medium and/or one or more additives such as in the instant disclosure, carnosine and/or other anti-senescence compounds.

Mammalian host cells, for example, Chinese hamster ovary (CHO) cells, can experience a reduction in viability nearing the end of a production run in a bioreactor. It has been discovered that the addition of an anti-senescence agent, such as carnosine and analogs thereof, to a cell culture medium helps maintain a higher viable cell number and cell viability until the protein is harvested.

In addition, methods for increasing productivity, such as altering the temperature after the growth phase and/or during the production phase of the production run may be used in accordance with the present invention. To give but one example, during the production of a protein product, specifically the antibody for growth differentiation factor-8 (GDF-8), the temperature was shifted downwards to help initiate and increase the productivity. In certain embodiments, addition of an anti-senescence compound such as carnosine helps increase the productivity of the cell culture. In certain embodiments, an anti-senescence compound may be added before, during and/or after such a temperature shift.

It has also been discovered that the addition of an anti-senescence compound such as carnosine to a cell culture medium increases the overall quality of protein product. During the production of the protein, high molecular weight aggregates, along with other unwanted species, are in the cell culture medium. The addition of carnosine decreases the amount of high molecular aggregates and increases product quality. In certain embodiments, addition of an anti-senescence compound other than carnosine decreases accumulation of such high molecular weight aggregates and improves product quality. In certain embodiments, carnosine is added in combination with one or more additional anti-senescence compounds.

The concentration of anti-senescence compound (e.g., carnosine) added to the cell culture medium can vary depending on many factors of the process, including, for example, the cell type, the desired product, and the conditions of the bioreactor, among others. Also, carnosine can be substituted with its analogues; acetyl-carnosine, homo-carnosine, anserine, and beta-alanine. In certain embodiments, carnosine is provided in combination with one or more other anti-senescence compounds. In certain embodiments, the concentration of anti-senescence agent (e.g., carnosine) in a cell culture medium is about 5 mM to about 100 mM. In certain embodiments, the concentration is about 10 mM to about 40 mM. In certain embodiments, the concentration is about 20 mM.

Any suitable culture procedures and inoculum medium may be used to culture the cells in the process of protein production. Both serum and serum free media may be used. In addition, culturing methods may be used to culture the cells as appropriate for the specific cell type and protein product. Such procedures are known and understood by those of ordinary skill in the cell culture art.

Other features and advantages of the disclosure will be apparent from the following description, and from the claims.

BRIEF DESCRIPTION OF THE DRAWINGS

FIG. 1a. Effect of Carnosine on Acidic Peaks for MYO-29.

FIG. 1b. Effect of Carnosine on High Molecular Weight Aggregates.

FIG. 1c. Effect of Carnosine Additions on Different Days on Acidic Peaks.

FIG. 1d. Effect of Carnosine Additions on Different Days on High Molecular Weight Aggregates.

FIG. 2a. Effect of Carnosine on Daily Viable Cell Density.

FIG. 2b. Effect of Carnosine on Daily Cell Viability.

FIG. 2c. Effect of Carnosine on Daily Titer.

FIG. 2d. Effect of Carnosine on Cumulative Specific Cellular Productivity. The bars on days 12 and 14 represent, from left to right: Control A D10 Feed, 20 mM Carnosine D10 Feed, Control B D10 Feed, 20 mM Carnosine (No D10 Feed), and Control C (No D10 Feed).

FIG. 2e. Effect of Carnosine on High Molecular Weight Aggregates. The bars on days 12 and 14 represent, from left to right: Control A D10 Feed, 20 mM Carnosine D10 Feed, Control B D10 Feed, 20 mM Carnosine (No D10 Feed), and Control C (No D10 Feed).

FIG. 3a. Effect of Different Concentrations of Carnosine on Viable Cell Density.

FIG. 3b. Effect of Different Concentrations of Carnosine on Daily Cell Viability.

FIG. 3c. Effect of Different Concentrations of Carnosine on Daily Titer.

FIG. 3d. Effect of Different Concentrations of Carnosine on Cumulative Specific Cellular Productivity. The bars represent, from left to right: Control P2, Control P5, 20 mM Carnosine, and 40 mM Carnosine.

FIG. 3e. Effect of Different Concentrations of Carnosine on High Molecular Weight Aggregates. The bars represent, from left to right: Control P2, Control P5, 20 mM Carnosine, and 40 mM Carnosine.

FIG. 4. Viable Cell Density Profiles of a Chinese Hamster Ovary (CHO) Cell Line Producing Recombinant TNFR Fusion Protein Grown in Media Containing or Lacking Carnosine. The Control Condition is the Average of 4 Control Bioreactor Runs.

FIG. 5. Cell Viability Profiles of a Chinese Hamster Ovary (CHO) Cell Line Producing Recombinant TNFR Fusion Protein Grown in Media Containing or Lacking Carnosine. The Control Condition is the Average of 4 Control Bioreactor Runs.

FIG. 6. Effect of Carnosine on the Percentage of Aggregated/Misfolded TNFR Fusion Protein. The Control Condition is the Average of 4 Control Bioreactor Runs.

FIG. 7. Effect of Carnosine on the Percentage of High Molecular Weight (HMW) Aggregates Produced by a Chinese Hamster Ovary (CHO) Cell Line Producing Recombinant TNFR Fusion Protein. The Control Condition is the Average of 4 Control Bioreactor Runs.

FIG. 8. Product Titer Profiles of a Chinese Hamster Ovary (CHO) Cell Line Producing Recombinant TNFR Fusion Protein Grown in Media Containing or Lacking Carnosine. The Control Condition is the Average of 4 Control Bioreactor Runs.

FIG. 9. Specific Cellular Productivity Profiles of a Chinese Hamster Ovary (CHO) Cell Line Producing Recombinant TNFR Fusion Protein Grown in Media Containing or Lacking Carnosine. The Control Condition is the Average of 4 Control Bioreactor Runs.

FIG. 10. Total Sialylation Profiles, Expressed as a Percentage of the Reference Material, of Recombinant TNFR Fusion Protein Produced by a Chinese Hamster Ovary (CHO) Cell Line Grown in Media Containing or Lacking Carnosine. The Control Condition is the Average of 4 Control Bioreactor Runs.

FIG. 11. Distribution of Sialylated N-linked Oligosaccharides, Expressed as a Percentage of Total N-Linked Oligosaccharides, of Recombinant TNFR Fusion Protein Produced by a Chinese Hamster Ovary (CHO) Cell Line Grown in Media Containing or Lacking Carnosine. The Control Condition is the Average of 4 Control Bioreactor Runs.

DEFINITIONS

Following long-standing convention, the terms "a" and "an" mean "one or more" when used in this application, including the claims. Even though the invention has been described with a certain degree of particularity, it is evident that many alternatives, modifications, and variations will be apparent to those skilled in the art in light of the disclosure. Accordingly, it is intended that all such alternatives, modifications, and variations, which fall within the spirit and scope of the invention, be embraced by the defined claims.

The term "anti-senescence compound" as used herein refers to any agent or compound that, when added to a cell culture, promotes viability, growth, and/or lifespan of a cell grown therein. In certain embodiments, use of such an anti-senescence compound in cell culture results in increased titer, increased cell specific productivity, increased cell viability, increased integrated viable cell density, decreased accumulation of high molecular weight aggregates, and/or decreased accumulation of acidic species than would be observed under otherwise identical culture conditions that lack the anti-senescence compound. Non-limiting examples of anti-senescence compounds that may be used in accordance with methods and compositions of the present invention include carnosine, acetyl-carnosine, homo-carnosine, anserine, and beta-alanine. In certain embodiments, two or more anti-senescence compounds may be used in accordance with compositions and methods of the present invention.

The phrase "host cell" refers to cells which are capable of being genetically manipulated and/or are capable of growth and survival in a cell culture medium. Typically, the cells can express a large quantity of an endogenous or heterologous protein of interest and can either retain the protein or secrete it into the cell culture medium Host cells are typically "mammalian cells," which comprise the nonlimiting examples of vertebrate cells, including baby hamster kidney (BHK), Chinese hamster ovary (CHO), human kidney (293), normal fetal rhesus diploid (FRhL-2), and murine myeloma (e.g., SP2/0 and NS0) cells. One of ordinary skill in the art will be aware of other host cells that may be used in accordance with methods and compositions of the present invention.

The term "cell culture medium" refers to a solution containing nutrients to support cell survival under conditions in which cells can grow and produce a desired protein. The phrases "inoculation medium" or "inoculum medium" refer to a solution or substance containing nutrients in which a culture of cells is initiated. In certain embodiments a "feed medium" contains similar nutrients as the inoculation medium, but is a solution or substance with which the cells are fed after initiation of the culture. In certain embodiments, a feed medium contains one or more components not present in an inoculation medium. In certain embodiments, a feed medium lacks one or more components present in an inoculation medium. A person of ordinary skill in the cell culture art will know without undue experimentation what components make-up the inoculation and feed mediums. Typically, these solutions provide essential and non-essential amino acids, vitamins, energy sources, lipids, and trace elements required by a cell for growth and survival. In certain embodiments, an inoculation medium, a feed medium or both comprise an anti-senescence compound.

The term "cell culture characteristic" as used herein refers to an observable and/or measurable characteristic of a cell culture. Methods and compositions of the present invention are advantageously used to improve one or more cell culture characteristics. In certain embodiments, improvement of a cell culture characteristic comprises increasing the magnitude of a cell culture characteristic. In certain embodiments, improvement of a cell culture characteristic comprises decreasing the magnitude of a cell culture characteristic. As non-limiting examples, a cell culture characteristic may be titer, cell specific productivity, cell viability, integrated viable cell density, accumulation of high molecular weight aggregates, and/or accumulation of acidic species. One of ordinary skill in the art will be aware of other cell culture characteristics that may be improved using methods and compositions of the present invention.

The term "defined medium" as used herein refers to a medium in which the composition of the medium is both known and controlled. Defined media do not contain complex additives such as serum or hydrolysates that contain unknown and/or uncontrolled components.

The term "complex medium" as used herein refers to a medium that contains at least one component whose identity or quantity is either unknown or uncontrolled.

The phrase "cell line" refers to, generally, primary host cells that express a protein of interest. In some embodiments, the cells have been transfected with exogenous DNA coding for a desired protein and/or containing control sequences that activate expression of linked sequences, whether endogenous or heterologous. In certain embodiments, cells derived from such genetically modified cells form a cell line and are placed in a cell culture medium to grow and produce the protein product. In certain embodiments, a cell line comprises primary host cells that have not been transfected with exogenous DNA and express an endogenous protein of interest.

The "growth phase" of a cell culture medium refers to the period when the cells are undergoing rapid division and growing exponentially, or close to exponentially. Typically, cells are cultured in conditions optimized for cell growth for generally 1-4 days. Growth phase conditions may include a temperature at about 35° C. to 42° C., generally about 37° C. The length of the growth phase and the culture conditions in the growth phase can vary but are generally known to a person of ordinary skill in the cell culture art. In certain embodiments, a cell culture medium in a growth phase is supplemented with a feed medium.

The "transition phase" occurs during the period when the cell culture medium is being shifted from conditions consistent with the growth phase to conditions consistent with the production phase. During the transition phase, factors like temperature, among others, are often changed. In certain embodiments, a cell culture medium in a transition phase is supplemented with a feed medium.

The "production phase" occurs after both the growth phase and the transition phase. The exponential growth of the cells has ended and protein production is the principal objective. The cell culture medium can be supplemented to initiate production. In certain embodiments, a cell culture medium in a production phase is supplemented with a feed medium. In addition, the temperature of the cell culture medium during the production phase may be lower, generally, than during the growth phase, which typically encourages production. The production phase continues until a desired endpoint is achieved.

The phrase "viable cell density" refers to the total number of cells that are surviving in the cell culture medium in a particular volume, generally per ml. The phrase "cell viability" refers to number of cells, which are alive compared to the total number of cells, both dead and alive, expressed as a percentage.

"Integrated Viable Cell Density", "IVCD": The terms "integrated viable cell density" or "IVCD" as used herein refer to the average density of viable cells over the course of the culture multiplied by the amount of time the culture has run. When the amount of protein produced is proportional to the number of viable cells present over the course of the culture, integrated viable cell density is a useful tool for estimating the amount of protein produced over the course of the culture.

The term "high molecular weight aggregates" refers to generally mis-folded proteins or an improper association of at least two polypeptides. The association may arise by any method including, but not limited to, covalent, non-covalent, disulfide, or nonreducible cross linking. In certain embodiments, methods and compositions of the present invention are advantageously utilized to reduce the accumulation of high molecular weight aggregates.

The phrase "antioxidant" refers to a compound that can prevent oxidative damage to lipids, proteins, DNA and other essential macromolecules by blocking free radicals.

"Therapeutic protein": A "therapeutic protein" is a protein or peptide that has a biological effect on a region in the body on which it acts or on a region of the body on which it remotely acts via intermediates. A therapeutic protein can be, for example, a secreted protein, such as, an antibody, an antigen-binding fragment of an antibody, a soluble receptor, a receptor fusion, a cytokine, a growth factor, an enzyme, or a clotting factor, as described in more detail herein below. The above list of proteins is merely exemplary in nature, and is not intended to be a limiting recitation. One of ordinary skill in the art will understand that any protein may be used in accordance with the present invention and will be able to select the particular protein to be produced based as needed.

As used in the specification, the terms polypeptide, protein and peptide are synonymous and are used interchangeably. Accordingly, as used herein, the size of a protein, peptide or polypeptide generally comprises more than 2 amino acids. For example, a protein, peptide or polypeptide can comprise from about 2 to about 20 amino acids, from about 20 to about 40 amino acids, from about 40 to about 100 amino acids, from about 100 amino acids to about 200 amino acids, from about 200 amino acids to about 300 amino acids, and so on.

As used herein, an amino acid refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

"Antibody": The term "antibody" is used to refer to any antibody-like molecule that has an antigen binding region, and includes antibody fragments such as Fab', Fab, F(ab').sub.2, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlow and Lane, Antibodies: A Laboratory Manual, Cold Spring Harbor Laboratory, 1988; incorporated herein by reference). For example, an antibody can include at least one, and preferably two full-length heavy chains, and at least one, and preferably two light chains. The term "antibody" as used herein includes an antibody fragment or a variant molecule such as an antigen-binding fragment (e.g., an Fab, F(ab')2, Fv, a single chain Fv fragment, a heavy chain fragment (e.g., a camelid VHH) and a binding domain-immunoglobulin fusion (e.g., SMIP™).

The antibody can be a monoclonal or single-specificity antibody. The antibody can also be a human, humanized, chimeric, CDR-grafted, or in vitro generated antibody. In yet other embodiments, the antibody has a heavy chain constant region chosen from, e.g., IgG1, IgG2, IgG3, or IgG4. In another embodiment, the antibody has a light chain chosen from, e.g., kappa or lambda. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). Typically, the antibody specifically binds to a predetermined antigen, e.g., an antigen associated with a disorder, e.g., a neurodegenerative, metabolic, inflammatory, autoimmune and/or a malignant disorder.

Small Modular ImmunoPharmaceuticals (SMIP™) provide an example of a variant molecule comprising a binding domain polypeptide. SMIPs and their uses and applications are disclosed in, e.g., U.S. Published Patent Application. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. According to one aspect of the invention, a single domain antibody as used herein is a naturally occurring single domain antibody known as heavy chain antibody devoid of light chains. Such single domain antibodies are disclosed in WO 9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized variable domain, e.g., a VHH domain; (vii) a single chain Fv (scFv); (viii) a bispecific antibody; and (ix) one or more fragments of an immunoglobulin molecule fused to an Fc region. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-26; Huston et al. (1988) Proc. Natl. Acad. Sci. U.S.A. 85:5879-83). Such single chain antibodies are also intended to be encompassed within the term "antigen-binding fragment" of an antibody. These antibody fragments are obtained using conventional techniques known to those skilled in the art, and the fragments are evaluated for function in the same manner as are intact antibodies.

Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The phrase "bioreactor" refers to a vessel in which a cell culture medium can be contained and internal conditions of which can be controlled during the culturing period, e.g., pH and temperature.

A "fed batch culture" refers to a method of culturing cells in which cells are first inoculated in a bioreactor with an inoculum medium. The cell culture medium is then supplemented at one or more points throughout the production run with a feed medium containing nutritional components and/or other supplements.

A "batch culture" refers to a method of culturing cells in which cells are inoculated in a bioreactor with all the necessary nutrients and supplements for the entirety of the production run. No nutrient additions are made to the cell culture medium throughout the duration of the production.

A "perfusion culture" refers to a method of culturing cells that is different from a batch or fed-batch culture method, in which the culture is not terminated, or is not necessarily terminated, prior to isolating and/or purifying an expressed protein of interest, and in which new nutrients and other components are periodically or continuously added to the culture, during which the expressed protein is periodically or continuously harvested. The composition of the added nutrients may be changed during the course of the cell culture, depending on the needs of the cells, the requirements for optimal protein production, and/or any of a variety of other factors known to those of ordinary skill in the art.

The phrase "expression" refers to the transcription and the translation that occurs within a host cell. The level of expression relates, generally, to the amount of protein being produced by the host cell.

"Cell specific productivity", and the like, refer to the specific, as in per cell, product expression rate. The cell specific productivity is generally measured in micrograms of protein produced per $10^6$ cells per day or in picograms of protein produced per $10^6$ cells per day.

The term "titer" as used herein refers to the total amount of recombinantly expressed protein produced by a cell culture in a given amount of medium volume. Titer is typically expressed in units of milligrams or micrograms of protein per milliliter of medium.

One of skill in the art will recognize that the methods disclosed herein may be used to culture many of the well-known mammalian cells routinely used and cultured in the art, i.e., the methods disclosed herein are not limited to use with only the instant disclosure.

DETAILED DESCRIPTION OF CERTAIN EMBODIMENTS OF THE INVENTION

It has been discovered that using an anti-senescence compound such as carnosine modifies the viability and productivity of a cell culture. For example, addition of carnosine maintains cell viability, and improves productivity of cells, and improves product quality of the desired protein product. Carnosine is an antioxidant and an anti-senescence compound that is also a naturally occurring dipeptide present at high levels (up to 20 mM) in muscle and nerve tissues in animals. Being an antioxidant, carnosine also is a free radical scavenger and glycation inhibitor. Generally, carnosine transforms reactive species into non-reactive species thereby protecting proteins, DNA, and other essential macromolecules. As an anti-senescence compound, carnosine can extend the lifespan of human diploid fibroblasts and human fetal lung (primary cell lines) at a concentration of 20 mM in culture media. The present invention encompasses the surprising finding that it is advantageous to use an anti-senescence compound (including, but not limited to, carnosine) in cell culture to produce a protein of interest. In certain embodiments, using such an anti-senescence compound in cell culture to produce a protein of interest results in one or more improved cell culture characteristics including, but not limited to, increased titer, increased cell specific productivity, increased cell viability, increased integrated viable cell density, decreased accumulation of high molecular weight aggregates, and/or decreased accumulation of acidic species.

It has been demonstrated that carnosine is cytotoxic to human or rodent transformed and neoplastic cells in Minimal Essential Medium (MEM, Sigma), which has lower glucose levels, but not in Dulbecco's Modified Eagle's Medium (DMEM, Sigma), which contains 1 mM pyruvate. (Holliday et al, *Biochemistry (Moscow)*, 65:843-848, 846). In addition, dialyzed fetal calf serum with low molecular weight compounds removed increased the cytotoxic effects of carnosine. Id. It was also determined that 1 mM oxaloacetate and 1 mM of α-ketoglutarate had comparable effects as pyruvate, neither of which are components of the inoculum or feed mediums used with the carnosine examples. Id. Sodium pyruvate, however, is an original component in the inoculum medium at a concentration of 0.5 mM, not for carnosine additions but rather to better mimic in vivo conditions in a bioreactor system and as a potential alternate energy source. The inoculum medium is also serum free, which would imply that carnosine would have cytotoxic effects. According to the reference, the addition of carnosine to a cell culture medium would have similar cytotoxic effects as seen in the MEM medium in Holliday. By utilizing methods and/or compositions of the present invention, such cytotoxicity is reduced or eliminated and cell viability and protein production are improved.

In certain embodiments, carnosine is provided in a cell culture medium at a concentration of between about 5 mM and about 100 mM. In certain embodiments, carnosine is provided in a cell culture medium at a concentration of about 10 mM to about 40 mM, for example at a concentration of about 20 mM. In certain embodiments, carnosine is provided in a cell culture medium at a concentration of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 mM, or higher. In certain embodiments, such concentrations of carnosine are achieved in cell culture by adding carnosine at multiple times during the cell culture process, for example, in one or more feed media. The concentration of carnosine utilized depends on the cell culture medium and the cell line being used, among other factors, including the desired effects being sought on the cell line or product. Analogs of carnosine, e.g. acetyl-carnosine, homo-carnosine, anserine, and beta-alanine, may also be provided in a cell culture medium for a similar effect. One or more of these analogs may be provided in a cell culture medium. In certain embodiments, such analogs are provided in a cell culture medium that lacks carnosine. In certain embodiments, such analogs are provided in a cell culture medium in combination with carnosine. In certain embodiments, such analogs are provided at a concentration of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 mM, or higher.

In certain embodiments, in order to produce a protein of interest, initially, host cells are transfected or transformed with exogenous DNA coding for a protein to supply transformed cells, which constitutively produce the desired protein product. In certain embodiments, a nucleic acid molecule introduced into the cell encodes the protein desired to be expressed according to the present invention. In certain embodiments, a nucleic acid molecule contains a regulatory sequence or encodes a gene product that induces or enhances the expression of the desired protein by the cell. As a non-limiting example, such a gene product may be a transcription factor that increases expression of the protein of interest.

In certain embodiments, a nucleic acid that directs expression of a protein is stably introduced into the host cell. In certain embodiments, a nucleic acid that directs expression of a protein is transiently introduced into the host cell. One of ordinary skill in the art will be able to choose whether to stably or transiently introduce the nucleic acid into the cell based on experimental, commercial or other needs.

A gene encoding a protein of interest may optionally be linked to one or more regulatory genetic control elements. In some embodiments, a genetic control element directs constitutive expression of the protein. In some embodiments, a genetic control element that provides inducible expression of a gene encoding the protein of interest can be used. Use of an inducible genetic control element (e.g., an inducible promoter) allows for modulation of the production of the protein in the cell. Non-limiting examples of potentially useful inducible genetic control elements for use in eukaryotic cells include hormone-regulated elements (see e.g., Mader, S, and White, J. H., Proc. Natl. Acad. Sci. USA 90:5603-5607, 1993), synthetic ligand-regulated elements (see, e.g. Spencer, D. M. et al., Science 262:1019-1024, 1993) and ionizing radiation-regulated elements (see e.g., Manome, Y. et al., Biochemistry 32:10607-10613, 1993; Datta, R. et al., Proc. Natl. Acad. Sci. USA 89:10149-10153, 1992). Additional cell-specific or other regulatory systems known in the art may be used in accordance with methods and compositions described herein.

Any host cell susceptible to cell culture, and to expression of proteins, may be utilized in accordance with the present invention. The host cells are generally mammalian cells, more particularly animal cells, such as Chinese hamster ovary (CHO) cells. Other non-limiting examples of mammalian cells that may be used in accordance with the present invention include BALB/c mouse myeloma line (NSO/I, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells+/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2).

Polypeptides

Any polypeptide that is expressible in a host cell may be produced in accordance with the present invention. The polypeptide may be expressed from a gene that is endogenous to the host cell, or from a heterologous gene that is introduced into the host cell. The polypeptide may be one that occurs in nature, or may alternatively have a sequence that was engineered or selected by the hand of man. A polypeptide to be produced according to the present invention may be assembled from polypeptide fragments that individually occur in nature. Additionally or alternatively, the engineered polypeptide may include one or more fragments that are not naturally occurring. Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Therapeutic proteins that may desirably be expressed in accordance with the present invention will often be selected on the basis of an interesting or useful biological or chemical activity. For example, the present invention may be employed to express any pharmaceutically or commercially relevant enzyme, clotting factor, receptor, antibody, hormone, regulatory factor, antigen, binding agent, etc. The following list of therapeutic proteins that can be produced according to the present invention is merely exemplary in nature, and is not intended to be a limiting recitation. One of ordinary skill in the art will understand that any polypeptide may be expressed in accordance with the present invention and will be able to select the particular polypeptide to be produced based on his or her particular needs.

Fusion Proteins

Fusion proteins generally have all or a substantial portion of a targeting peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. A fusion protein can include a targeting moiety, e.g., a soluble receptor fragment or a ligand, and an immunoglobulin chain, an Fc fragment, a heavy chain constant regions of the various isotypes, including for example: IgG1, IgG2, IgG3, IgG4, IgM, IgA1, IgA2, IgD, and IgE. For example, the fusion protein can include the extracellular domain of a receptor, and, e.g., fused to, a human immunoglobulin Fc chain (e.g., human IgG1 or human IgG4, or a mutated form thereof). In one embodiment, the human Fc sequence has been mutated at one or more amino acids, e.g., mutated at residues 254 and 257 from the wild type sequence to reduce Fc receptor binding. The fusion proteins may additionally include a linker sequence joining the first moiety to the second moiety, e.g., the immunoglobulin fragment. For example, the fusion protein can include a peptide linker, e.g., a peptide linker of about 4 to 20, more preferably, 5 to 10, amino acids in length; in certain embodiments, the peptide linker is 8 amino acids in length. For example, the fusion protein can include a peptide linker having the formula (Ser-Gly-Gly-Gly-Gly)y wherein y is 1, 2, 3, 4, 5, 6, 7, or 8. In other embodiments, additional amino acid sequences can be added to the N- or C-terminus of the fusion protein to facilitate expression, steric flexibility, detection and/or isolation or purification.

Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

Antibodies

Antibodies are proteins that have the ability to specifically bind a particular antigen. Given the large number of antibodies currently in use or under investigation as pharmaceutical or other commercial agents, production of antibodies in accordance with the present invention is of particular interest. For example, the present invention may be used to produce antibodies in a cell culture wherein the misfolding and/or aggregation of the produced antibodies are reduced.

In certain embodiments, methods and/or compositions of the present invention are employed to produce an antibody against growth differentiation factor-8 (GDF-8). Nonlimiting examples of GDF-8 antibodies include Myo29, Myo28, and Myo22. In certain embodiments, GDF-8 antibodies produced in accordance with the present teachings are produced in the form of human IgG isotopes. In certain embodiments, methods and/or compositions of the present invention are employed to produce a MYO29 antibody such as described in international patent application, publication number WO 2004/037861, entitled Neutralizing Antibodies Against GDF-8 and Uses Thereof, incorporated herein by reference in its entirety.

Other representative commercially available therapeutic proteins that can be produced in accordance with the present invention include, for example, AVASTIN [Bevacizumab], CAMPATH [Alemtuzumab], ERBITUX [Cetuximab], HERCEPTIN [TRASTUZUMAB], HUMIRA [Adalimumab], LUCENTIS [Ranibizumab], MYLOTARG [gemtuzumab ozogamicin], MYCSCINT [Imicromab Penetate], PROSTASCINT [Capromab Pendetide], RAPTIVA [Efalizumab], REMICADE [Infliximab], REOPRO [Abciximab], RITUXAN [Rituximab], SIMULECST [Basilximab], SOLIRIS [Eculizumab], SYNAGIS [Palivizumab], TYSABRI [Natalizumab], VECTIBIX [Panitumumab], VERLUMA [Nofetumomab], XOLAIR [Omalizumab], ZANAPAX [Daclizumab], ZEVALIN [Ibritumomab Tiuxetan], etc.

In certain embodiments, the monoclonal, chimeric, or humanized antibodies described above contain amino acid residues that do not naturally occur in any antibody in any species in nature. These foreign residues can be utilized, for example, to confer novel or modified specificity, affinity or effector function on the monoclonal, chimeric or humanized antibody.

Clotting Factors

Clotting factors have been shown to be effective as pharmaceutical and/or commercial agents. Hemophilia B is a disorder in which the blood of the sufferer is unable to clot. Thus, any small wound that results in bleeding is potentially a life-threatening event. Given the importance of recombinant clotting factors in the treatment of diseases such as hemophilia, production of clotting factors in accordance with the present invention is of particular interest. In certain embodiments, the present invention may be used to produce clotting factors in a cell culture wherein the misfolding and/or aggregation of the produced clotting factors are reduced.

For example, Coagulation Factor IX (Factor IX or "FIX") is a single-chain glycoprotein whose deficiency results in Hemophilia B. FIX is synthesized as a single chain zymogen that can be activated to a two-chain serine protease (Factor IXa) by release of an activation peptide. The catalytic domain of Factor IXa is located in the heavy chain (see Chang et al., J. Clin. Invest., 100:4, 1997, incorporated herein by reference in its entirety). Other clotting factors that can be produced in accordance with the present invention include tissue factor, and von Willebrands factor and/or commercially available blood-clotting factors. Representative commercially available blood-clotting factors that can be produced in accordance with the present invention include, for example, ALTEPLASE [Tissue Plasminogen Activator; t-PA], BENEFIX [Factor IX], HEMOFIL [Antihemophilic Factor; Factor XIII], RECOMBINATE (Recombinant Antihemophiliac Factor), etc.

Enzymes

Another class of polypeptides that have been shown to be effective as pharmaceutical and/or commercial agents and that can desirably be produced according to the teachings of the present invention includes enzymes. Given the importance of recombinant enzymes in the treatment of diseases and other commercial and pharmaceutical uses, production of enzymes in accordance with the present invention is of particular interest. For example, the present invention may be used to produce enzymes in a cell culture wherein the misfolding and/or aggregation of the produced enzymes are reduced. Representative commercially available enzymes that can be produced in accordance with the present invention include, for example, ACTIVASE [Recombinant alteplase], CEREDASE [Alglucerase], CEREZYME [Imiglucerase], PULMOZYME [DNase], etc.

Growth Factors and Other Signaling Molecules

Another class of polypeptides that have been shown to be effective as pharmaceutical and/or commercial agents and that can desirably be produced according to the teachings of the present invention includes growth factors and other signaling molecules. Growth factors are often glycoproteins that are secreted by cells and bind to and activate receptors on other cells, initiating a metabolic or developmental change in the receptor cell. Given the biological importance of growth factors and other signaling molecules and their importance as potential therapeutic agents, production of these molecules in accordance with the present invention is of particular interest. For example, the present invention may be used to produce growth factors or other signaling molecules in a cell culture wherein the misfolding and/or aggregation of the produced growth factors or other signaling molecules are reduced.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin (representative commercially available erythropoietins include, for example, ARANESEP [darbepoetin]; CEA-SCAN [Arcitumomab], EPOGEN [epoetin alfa]; PROCRIT [epoetin alfa]), etc.); osteoinductive factors; immunotoxins; a bone morphogenetic protein (BMP); an interferon such as interferon-alpha, -beta, and -gamma (representative commercially available interferons include, for example, ACTIMUNNE [Interferon gamma-1b], AVONEX [Interferon beta-1a], REBIF [Interferon beta-1a], BETASE-RON [Interferon beta-1b]), etc.); colony stimulating factors (CSFs), e.g., M-CSF, GM-CSF, and G-CSF (other representative commercially available colony stimulating factors include, for example, GRANOCYTE [Lenograstim], LEUKINE [Sargramostim], etc.); interleukins (ILs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with methods and compositions of the present invention.

Receptors

Another class of polypeptides that have been shown to be effective as pharmaceutical and/or commercial agents and that can desirably be produced according to the teachings of the present invention includes receptors. Given the biological importance of receptors and their importance as potential therapeutic agents, production of these molecules in accordance with the present invention is of particular interest. For example, the present invention may be used to produce receptors in a cell culture wherein the misfolding and/or aggregation of the produced receptors are reduced.

Receptors are typically trans-membrane glycoproteins that function by recognizing an extra-cellular signaling ligand. Receptors often have a protein kinase domain in addition to the ligand recognizing domain. This protein kinase domain initiates a signaling pathway by phosphorylating target intracellular molecules upon binding the ligand, leading to developmental or metabolic changes within the cell. In certain embodiments, an extracellular domain of a transmembrane receptor is produced in accordance with methods and systems disclosed herein. In certain embodiments, an intracellular domain of a transmembrane receptor is produced in accordance with methods and systems disclosed herein.

In certain embodiments, tumor necrosis factor inhibitors, in the form of tumor necrosis factor alpha and beta receptors (TNFR-1; EP 417,563 published Mar. 20, 1991; and TNFR-2, EP 417,014 published Mar. 20, 1991, each of which is incorporated herein by reference in its entirety) are expressed in accordance with systems and methods of the present invention (for review, see Naismith and Sprang, J. Inflamm. 47(1-2):1-7, 1995-96, incorporated herein by reference in its entirety). According to some embodiments, a tumor necrosis factor inhibitor comprises a soluble TNF receptor. In certain embodiments, a tumor necrosis factor inhibitor comprises a soluble TNFR fused to any portion of an immunoglobulin protein, including the Fc region of an immunoglobulin. In certain embodiments, TNF inhibitors of the present invention are soluble forms of TNFR I and TNFR II. In certain embodiments, TNF inhibitors of the present invention are soluble TNF binding proteins. In certain embodiments, the TNF inhibitors of the present invention are TNFR-Fc, for example, etanercept. As used herein, "etanercept," refers to a TNFR-Fc, which is a dimer of two molecules of the extracellular portion of the p75 TNF-α receptor, each molecule consisting of a 235 amino acid Fc portion of human IgG1. In accordance with the invention, an anti-senescence compound, such as carnosine, is used to decrease the amount of misfolded and/or aggregated protein during the production of TNFR-Fc.

In some embodiments, receptors to be produced in accordance with the present invention are receptor tyrosine kinases (RTKs). The RTK family includes receptors that are crucial for a variety of functions numerous cell types (see, e.g., Yarden and Ullrich, Ann. Rev. Biochem. 57:433-478, 1988; Ullrich and Schlessinger, Cell 61:243-254, 1990, each of which is incorporated herein by reference). Non-limiting examples of RTKs include tumor necrosis factor alpha and beta receptors, members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., Nature 376(6535):70-74, 1995, incorporated herein by reference in its entirety) and c-Met receptor, some of which have been suggested to promote angiogenesis, directly or indirectly (Mustonen and Alitalo, J. Cell Biol. 129:895-898, 1995). Other non-limiting examples of RTK's include fetal liver kinase 1 (FLK-1) (sometimes referred to as kinase insert domain-containing receptor (KDR) (Terman et al., Oncogene 6:1677-83, 1991) or vascular endothelial cell growth factor receptor 2, VEGFR-2), fms-like tyrosine kinase-1 (Flt-1) (DeVries et al. Science 255; 989-991, 1992; Shibuya et al., Oncogene 5:519-524, 1990), sometimes referred to as vascular endothelial cell growth factor receptor 1 (VEGFR-1), neuropilin-1, endoglin, endosialin, and Axl. Those of ordinary skill in the art will be aware of other receptors that can be expressed in accordance with the present invention.

In certain embodiments, the receptor to be produced in accordance with the present invention is a G-protein coupled receptor (GPCR). GPCRs are a major target for drug action and development. In fact, receptors have led to more than half of the currently known drugs (Drews, Nature Biotechnology, 14:1516, 1996) and GPCRs represent the most important target for therapeutic intervention with 30% of clinically prescribed drugs either antagonizing or agonizing a GPCR (Milligan, G. and Rees, S., TIPS, 20:118-124, 1999). Since these receptors have an established, proven history as therapeutic targets, production of GPCRs in accordance with the present invention is also of particular interest.

In general, practitioners of the present invention will select their protein or polypeptide of interest, and will know its precise amino acid sequence. Any given polypeptide that is to be expressed in accordance with the present invention will have its own particular characteristics and may influence the cell density or viability of the cultured cells, and may be expressed at lower levels than another polypeptide or protein grown under identical culture conditions. One of ordinary skill in the art will be able to appropriately modify inventive media and methods described herein in order to optimize cell growth, titer, folding or any other property of a given expressed polypeptide or protein.

One of ordinary skill in the art will be aware of other useful and/or desirable proteins that may be expressed in accordance with methods and compositions of the present invention.

Cell lines may be cultured using a variety of techniques to produce the desired protein product. The cell culture can be done on a small or large scale, depending on the purpose of the cell culture medium or use of the product. For example, cells may be grown in a bioreactor. In certain embodiments, the volume of the bioreactor is at least 1 liter and may be 10, 100, 250, 500, 1,000, 2,500, 5,000, 8,000, 10,000, 12,000 liters or more, or any volume in between. In addition, bioreactors that may be used include, but are not limited to, a stirred tank bioreactor, fluidized bed reactor, hollow fiber bioreactor, or roller bottle. The systems can also operate either in a batch, fed-batch, or continuous/perfusion mode. The bioreactor and mode in which to control and monitor the cell culture medium will be known to one of ordinary skill in the cell culture art. In the instant example, the system utilized is a stirred tank bioreactor and operated in fed-batch mode.

The bioreactor is generally seeded with an inoculum medium and a chosen cell line, for example a TNFR fusion protein cell line, which may be transfected to stably express and produce the desired protein product. Commercially available medium such as Minimal Essential Medium (MEM, Sigma), Ham's F10 (Sigma), or Dulbecco's Modified Eagle's Medium (DMEM, Sigma) may be used as the base medium. These base mediums may then be supplemented with amino acids, vitamins, trace elements, and/or other components to produce the inoculum or feed mediums used during the production run. In certain embodiments, a base medium is altered to permit robust growth of cells, to increase cell viability, to increase cell productivity, to increase integrated viable cell density, and/or to improve the quality of the produced protein in the presence of carnosine. For example, a base medium may be supplemented with pyruvate, oxaloacetate and/or α-ketoglutarate. One of ordinary skill in the art will be able to alter a base medium for use with methods and compositions of the present invention without undue experimentation.

In certain embodiments, cells are cultured in any of a variety of chemically defined media containing an anti-senescence compound, wherein the components of the media are both known and controlled. For example, defined media typically do not contain complex additives such as serum or hydrolysates. In certain embodiments, cells are cultured in any of a variety of complex media containing an anti-senescence compound, in which not all components of the medium are known and/or controlled. In certain embodiments, such an anti-senescence compound comprises carnosine.

The conditions of the bioreactor are controlled typically, with the pH set between about 6.5 to about 7.5. The pH is adjusted using an acid, generally $CO_2$, or a base, such as sodium bicarbonate. The dissolved oxygen is controlled between about 5 and 90% of air saturation, and the temperature is held between 30° C. to 42° C., during the growth phase. A person of ordinary skill in the cell culture art can modify the conditions of the bioreactor based upon the cell line and methods being employed to achieve the desired results without undue experimentation.

Compositions and methods of the present invention may be used with any cell culture method or system that is amenable to the expression of proteins. For example, cells expressing a protein of interest may be grown in batch or fed-batch cultures, wherein the culture is terminated after sufficient expression of the protein, after which the expressed protein is harvested and optionally purified. Alternatively, cells expressing a protein of interest may be grown in perfusion cultures, wherein the culture is not terminated and new nutrients and other components are periodically or continuously added to the culture, during which the expressed protein is periodically or continuously harvested.

After the cells are seeded they go through a growth phase during which the number of cells generally increases exponentially. During the growth phase, the temperature or temperature range of the cell culture will be selected based primarily on the temperatures or range of temperatures at which the cell culture remains viable, at which a high level of protein is produced, at which production or accumulation of metabolic waste products is minimized, and/or any combination of these or other factors deemed important by the practitioner. As one non-limiting example, CHO cells grow well and produce high levels or protein at approximately 37° C. In general, most mammalian cells grow well and/or can produce high levels or protein within a range of about 25° C. to 42° C., although methods taught by the present disclosure are not limited to these temperatures. Certain mammalian cells grow well and/or can produce high levels of protein within the range of about 35° C. to 40° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times during the growth phase. Those of ordinary skill in the art will be able to select appropriate temperature or temperature range in which to grow cells, depending on the needs of the cells and the production requirements of the practitioner.

Following the growth phase is a transition phase during which the cells adapt to any changes occurring in the surroundings, such as a temperature change. The changes occurring are typically parameters for the production phase. In the instant examples, on day 4, the temperature decreased from about 37° C. to about 31° C. The temperature shift, however, can occur more than once and does not need to necessarily go in the downward direction. Moreover, the transition phase and the temperature shift can occur on any day during the production run. Although most methods of production include multi-phase processes, carnosine also may be utilized in a single-phase process.

When shifting the temperature of the culture, the temperature shift may be relatively gradual. For example, it may take several hours or days to complete the temperature change. Alternatively, the temperature shift may be relatively abrupt. The temperature may be steadily increased or decreased during the culture process. Alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple discrete temperature shifts are encompassed in these embodiments. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

Finally, there is the production phase where the cell number does not substantially increase, but rather the cells produce the desired protein product. One of ordinary skill in the art will understand, however, that in certain embodiments, cells may continue to grow and increase in number during the production phase. During this phase the environment of the bioreactor is controlled at conditions in which the cells are more likely to be productive. For example, the temperature is generally held at a temperature different than that of the growth phase, which is conducive to the production of a protein product, e.g. 31° C. Throughout the production run, the cells may be fed a feed medium containing nutrients and supplements the cells may need. For example, in certain cases, it may be beneficial or necessary to supplement the cell culture during the subsequent production phase with nutrients or other medium components that have been depleted or metabolized by the cells. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source. These supplementary components may all be added to the cell culture at one time, or they may be provided to the cell culture in a series of additions. In certain embodiments, an anti-senescence compound is provided in a feed medium at one or more times during the production phase.

According to certain embodiments, use of an anti-senescence compound, e.g. carnosine, in the cell culture medium during the production phase, whether provided in an inoculation medium or a feed medium, increases cell viability and/or specific protein production, thus improving the overall yield of produced protein.

Aspects of a protein production process are determined by one of ordinary skill in the cell culture art. The parameters such as seed density, duration of the production culture, operating conditions during harvest, among others, including those mentioned above are functions of the cell line and the cell culture medium. Therefore, the parameters can be determined without undue experimentation by a person of ordinary skill in the cell culture art.

As with the temperature or temperature range during the growth phase, the temperature or temperature range of the cell culture during the production phase will be selected based primarily on the temperature or temperature range at which the cell culture remains viable, at which a high level of protein is produced, at which production or accumulation of metabolic waste products is minimized, and/or any combination of these or other factors deemed important by the practitioner. In general, most mammalian cells remain viable and produce high levels or protein within a range of about 25° C. to 42° C., although methods taught by the present disclosure are not limited to these temperatures. In certain embodiments, mammalian cells remain viable and produce high levels or protein within a range of about 25° C. to 35° C. In certain embodiments, the cell culture is grown at a temperature of 20, 21, 22, 23, 24, 25, 26, 27, 28, 29, 30, 31, 32, 33, 34, 35, 36, 37, 38, 39, 40, 41, 42, 43, 44, or 45° C. at one or more times during the production phase. Those of ordinary skill in the art will be able to select appropriate temperature(s) or temperature range(s) in which to grow cells during the production phase, depending on the particular needs of the cells and the particular production requirements of the practitioner. The cells may be grown for any amount of time, depending on the needs of the practitioner and the requirement of the cells themselves.

In certain embodiments, batch or fed-batch cultures are terminated once the culture achieves one or more relevant culture conditions, as determined by the needs of the practitioner. In certain embodiments, batch or fed-batch cultures are terminated once the expressed protein reaches a sufficiently high titer, once the cell density reaches a sufficiently high level, once the expressed protein reaches a sufficiently high cell density, and/or to prevent undesirable production or accumulation of metabolic waste products (e.g., lactate and/or ammonium). One of ordinary skill in the art will be aware of other relevant culture conditions that may be used to determine when a batch or fed-batch culture should be terminated, based on experimental, commercial, and/or other considerations.

In certain embodiments, following a production run, the protein product is recovered from the cell culture medium and further isolated using traditional separation techniques. For example, the protein may initially be separated by centrifugation, retaining the supernatant containing the protein. Additionally or alternatively, the protein product may be bound to the surface of the host cell. In such embodiments, the media is removed and the host cells expressing the protein are lysed as a first step in the purification process. Lysis of mammalian host cells can be achieved by any number of means known to those of ordinary skill in the art, including physical disruption by glass beads and exposure to high pH conditions.

Using conventional protein purification methods, the protein may be additionally isolated. Methods by which to isolate and purify the desired protein product are known within the cell culture art. Specific methods depend on the cell line used and the product sought.

The anti-senescence compound, e.g. carnosine, may be added to the culture medium at a time optimal for the specific cell culture process. For the instant examples, the addition of carnosine occurs after the growth phase is substantially complete and is in the transition phase. During the addition, the cell culture medium is adapting to the new temperature resulting from the temperature shift. The transition phase is generally when agents are added to help initiate the production phase. Carnosine, however, may be added at any point during the production run that generates optimal results, including the growth phase and the production phase. Carnosine may also be added in combination with other components, such as a feed medium. In certain embodiments, an anti-senescence compound is provided in an inoculation medium and is present in the cell culture during the entire cell culture process. In certain embodiments, two or more anti-senescence compounds are provided in the cell culture medium. In certain embodiments, two or more anti-senescence compounds are provided in an inoculation medium and are present in the cell culture during the entire cell culture process. In certain embodiments, two or more anti-senescence compounds are provided, wherein one anti-senescence compound is provided in an inoculation medium and is present in the cell culture during the entire cell culture process, while another anti-senescence compound is provided after the cell culture has begun.

In certain embodiments, the concentration of an anti-senescence compound present in the cell culture is different for varying cell types and products. In certain embodiments, the concentration of carnosine present is different for varying cell types and products. Generally, the concentration is enough to enhance the productivity and quality without toxic effects. For the instant examples, the range includes, but is not limited to, 5 mM to 100 mM. It will be appreciated that the concentration of carnosine used may vary depending on the cell culture medium. The appropriate concentration of carnosine for a particular cell line may need to be determined with routine small-scale experiments, such as, for example, a 2 L bioreactor, using conventional methods. One of ordinary skill in the art will be able to determine an advantageous or optimal concentration of carnosine or other anti-senescence compound without undue experimentation using cell culture techniques and diagnostic methods that are known in the art.

One advantage to adding carnosine or another anti-senescence compound, rather than chemical agents, is the effect on viability. Typically, cell growth ceases and the viable cell number decreases with the addition of a chemical agent, like sodium butyrate. (Kim et al. *Biotechnol Bioeng*, 71: 184-193, 184). Examples below, however, demonstrate that addition of carnosine to a cell culture medium results in higher viability at the time of harvest than is observed in a cell culture grown in the absence of an anti-senescence compound such as carnosine. Furthermore, such carnosine-containing cell cultures exhibit an increase in specific productivity. With the positive effects on the cell viability and specific productivity, the overall yield is higher.

Another advantage is that an anti-senescence compound such as carnosine decreases the amount of high molecular weight aggregates and/or the number of acidic species. Decreasing the amount of high molecular weight aggregates and acidic species simplifies purification of the protein product. Enabling the protein to be isolated more efficiently decreases the cost to produce the protein product. In certain embodiments, an anti-senescence compound, such as carnosine, is used to decrease the amount of misfolded and/or aggregated protein. In certain embodiments, an anti-senescence compound other than carnosine is used to decrease the amount of high molecular weight aggregates and/or acidic species. In certain embodiments, two or more anti-senescence compounds are used to decrease the amount of high molecular weight aggregates and/or acidic species.

In certain embodiments, cells are grown in accordance with any of the cell culture methods described in U.S. patent application Ser. Nos. 11/213,308, 11/213,317 and 11/213,633 each of which was filed Aug. 25, 2005, and each of which is herein incorporated by reference in its entirety. For example, in certain embodiments, the cells may be grown in a culture medium in which the cumulative amino acid concentration is greater than about 70 mM. In certain embodiments, the cells may be grown in a culture medium in which the molar cumulative glutamine to cumulative asparagine ratio is less than about 2. In certain embodiments, the cells may be grown in a culture medium in which the molar cumulative glutamine to cumulative total amino acid ratio is less than about 0.2. In certain embodiments, the cells may be grown in a culture medium in which the molar cumulative inorganic ion to cumulative total amino acid ratio is between about 0.4 to 1. In certain embodiments, the cells may be grown in a culture medium in which the combined cumulative glutamine and cumulative asparagine concentration is between about 16 and 36 mM. In certain embodiments, the cells may be grown in a culture medium that contains two, three, four or all five of the preceding medium conditions. Use of such media allows high levels of protein production and lessens accumulation of certain undesirable factors such as ammonium and/or lactate.

In some embodiments, the cells are grown under one or more of the conditions described in U.S. Provisional Patent Application Ser. No. 60/830,658, filed Jul. 13, 2006 and incorporated herein by reference in its entirety. For example, in some embodiments, cells are grown in a culture medium that contains manganese at a concentration between approximately 10 and 600 nM. In some embodiments, cells are grown in a culture medium that contains manganese at a concentration between approximately 20 and 100 nM. In some embodiments, cells are grown in a culture medium that contains manganese at a concentration of approximately 40 nM. Use of such media in growing glycoproteins results in production of a glycoprotein with an improved glycosylation pattern (e.g. a greater number of covalently linked sugar residues in one or more oligosaccharide chains).

In certain embodiments of the invention, proteins produced according to one or more methods of the present invention will have pharmacologic activity and will be useful in the preparation of pharmaceuticals. Proteins produced according to one or more methods of the present invention may be administered to a subject or may first be formulated for delivery by any available route including, but not limited to parenteral (e.g., intravenous), intradermal, subcutaneous, oral, nasal, bronchial, opthalmic, transdermal (topical), transmucosal, rectal, and vaginal routes. Inventive pharmaceutical compositions typically include a purified protein expressed from a mammalian cell line, a delivery agent (i.e., a cationic polymer, peptide molecular transporter, surfactant, etc., as described above) in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Such formulations will be known by those of skill in the art. In certain embodiments, a protein produced according to the present invention is formulated in oral and/or parenteral form. In certain embodiments, for ease of administration and uniformity of dosage, such oral and/or parenteral forms are formulated as unit dosage form, wherein each unit contains a predetermined quantity of active protein calculated to produce the desired therapeutic effect in association with the required pharmaceutical carrier. One of ordinary skill in the art will be aware of unit dosage formulations appropriate for proteins produced according to the present invention.

Certain embodiments and aspects are discussed in detail above. The present disclosure is further illustrated by the following, non-limiting examples. Those of ordinary skill in the art will understand, however, that various modifications to these embodiments are within the scope of the appended claims. It is noted that the addition of carnosine and/or other anti-senescence compounds is equally applicable to other mammalian cell cultures and protein products. It is the claims and equivalents thereof that define the scope of the present invention, which is not and should not be limited to or by this description of certain embodiments.

EXAMPLES

Example 1

Dish Scale Carnosine Experiments

A MYO-29 cell line was cultured in a serum free production medium in a bioreactor with a 1 L working volume and was temperature shifted from 37° C. to 31° C. on day 4. The pH of the bioreactor was held at 7.00 and the dissolved oxygen was at 30% air saturation. Cell culture medium was then taken from the bioreactor on day 4, day 7, and day 10 and put into culture dishes with an 8 ml working volume and placed into a 31° C. incubator, where the dish cultures were cultured until day 12. The cells were supplemented with a feed medium on days 5 and 7. On day 5, 10% (v/v) of feed medium was added to the cell cultures and on day 7, 5%

(v/v) of feed medium was added to the cell cultures. 10 mM of carnosine was added on day 4, day 7, and day 10, respectively, to the dishes and the cell culture medium was harvested on day 12.

FIG. 1a shows the effect of the carnosine additions on the amount of acidic peaks in the culture on day 7. FIG. 1b shows the effect of the carnosine on the high molecular weight aggregates on the day 7 culture. FIG. 1c illustrates the effect of carnosine additions on day 4, versus day 7, versus day 10 on the acidic peaks. FIG. 1d shows the same experiment's results but for high molecular weight aggregates. Overall, carnosine had a positive effect by decreasing both the acidic peaks and the high molecular weight aggregates in cultured dishes.

Example 2

Effects of Carnosine Addition to Cell Culture Medium

Five bioreactors were inoculated with $0.9 \times 10^6$ cells/ml with a 1 L working volume of a MYO-29 cell line in a serum free inoculation medium. All the bioreactors were fed 5% (v/v) of a feed medium on days 3, 5, 7, and 12 of a 14-day run. A day 10 feed of 5% (v/v) of the feed medium was added to two of the control bioreactors and one containing carnosine. The conditions of the bioreactors were held at a temperature of 37° C., a pH of 7.00, and a dissolved oxygen level at 30% air saturation. The agitation rate was 200 rpm and the sparge gas had a combination of air and 7% carbon dioxide.

All cells were cultured for 4 days at which point 20 mM of carnosine was added to two of the bioreactors, the controls did not have carnosine added, and the temperature was shifted to 31° C. in all of the bioreactors on day 4 also. The bioreactors were harvested on day 14 of the production run. Samples were taken throughout the run to monitor the progress of the cell culture medium. The controls performed as expected.

FIG. 2a shows the daily viable cell density. FIG. 2b shows that the daily cell viability of the bioreactors with carnosine was higher upon being harvested compared to two bioreactors without it. FIG. 2c shows the daily titer of the bioreactors and that the two bioreactors with carnosine present had higher titer at the time of harvest. The cultures with carnosine had better cumulative specific cellular productivity shown in FIG. 2d. FIG. 2e shows the amount of high molecular weight aggregates and shows a decrease of high molecular weight aggregates in the bioreactors with carnosine present.

Example 3

Effect of Different Concentration of Carnosine Additions

Four bioreactors were inoculated with $0.4 \times 10^6$ cells/ml with a 1 L working volume of a MYO-29 cell line in a serum free inoculation medium. All the bioreactors were all fed 5% (v/v) of a feed medium on day 7 of the 14-day run. The conditions of the bioreactor were held at a temperature of 37° C., a pH of 7.00, and a dissolved oxygen level at 30% air saturation. The agitation rate was 200 rpm and the sparge gas had a combination of air and 7% carbon dioxide.

All cells were cultured for four days at which point the temperature was shifted in all of the bioreactors to 31° C. Also on day 4, 20 mM of carnosine was added to one bioreactor, a second had 40 mM of carnosine added, and the controls did not have any carnosine added. All bioreactors were harvested on day 12 of the production run. Samples were taken throughout the run to monitor the progress of the cell culture medium. The controls performed generally as expected, except one control had slightly lower daily viabilities than previously seen.

FIG. 3a shows the daily viable cell density, the different bioreactors are fairly similar with the exception of the bioreactor with 4 mM of carnosine. FIG. 3b shows that the daily cell viability of the bioreactors with carnosine had a higher viability upon being harvested compared to two control bioreactors without it. FIG. 3c shows the daily titer; the bioreactors with the carnosine additions and one of the controls were similar. The bioreactor with 40 mM of carnosine had a higher cumulative specific cellular productivity. (FIG. 3d). FIG. 3e shows the amount of high molecular weight aggregates; overall there is a decrease in high molecular weight aggregates with the carnosine additions compared to the controls.

Example 4

Use of Carnosine in Mammalian Cell Culture to Improve Product Characteristics of a Recombinant TNFR Fusion Protein A TNFR fusion protein cell line was cultured in a serum free production medium in a bioreactor with a 1 L working volume. On day 1, the temperature was shifted from 37° C. to 29.5° C., sodium butyrate was added to a final concentration of 1 mM, and HMBA was added to a final concentration of 3 mM. The pH of the bioreactor was held at 6.95 and the dissolved oxygen was at 60% air saturation. On day 2, carnosine was added to the culture to a final concentration of 20 mM. The cells were supplemented with a 5% (v/v) feed medium on days 3, 6, 8, and 10. The cell culture medium was harvested on day 12. Four separate control bioreactors were run in which CHO cells expressing a recombinant TNFR fusion protein were grown under conditions identical to those described above, except that carnosine was not added on day 2. The control data in FIGS. 4-11 is the average of the four control bioreactor runs.

As can be seen in FIGS. 4 and 5, cell growth and cell viability were not significantly affected by carnosine addition. FIG. 6 shows that the amount of misfolded and/or aggregated TNFR fusion protein, as measured by hydrophobic interaction chromatography (HIC), was significantly reduced when the cells were grown in media containing carnosine. FIG. 7 shows that the amount of high molecular weight (HMW) aggregates, as measured by size exclusion chromatography (SEC), was also significantly reduced when cells expressing TNFR fusion protein were grown in media containing carnosine. FIGS. 8 and 9 show that product titer and specific cellular productivity, respectively, were increased when cells expressing TNFR fusion protein were grown in media containing carnosine. Finally, FIGS. 10 and 11 show that glycosylation of the produced TNFR fusion protein was not significantly different when the cells were grown in media containing carnosine.

Although the some embodiments of the disclosure have been described herein, the above description is merely illustrative. Further modification of the embodiments herein disclosed will occur to those skilled in the cell culture art and all such modifications are deemed to be within the scope of the embodiments as defined by the appended claims.

What is claimed is:

1. A method of producing a TNFR fusion protein in cell culture comprising steps of:
   culturing mammalian cells that contain a gene encoding the TNFR fusion protein, which gene is expressed under conditions of cell culture, in a cell culture medium comprising an anti-senescence compound, wherein the anti-senescence compound is selected from the group consisting of carnosine, acetyl-carnosine, homo-carnosine, anserine, and beta-alanine and combinations thereof; and
   maintaining the culture under conditions and for a time sufficient to permit expression of the protein; and
   harvesting the cell culture medium, which contains the protein;
   and wherein the mammalian cells are Chinese hamster ovary (CHO) cells.

2. The method of claim 1, wherein the anti-senescence compound comprises carnosine.

3. The method of claim 1, wherein the anti-senescence compound is present in the cell culture medium at a concentration of between about 5 mM and about 100 mM.

4. The method of claim 1, wherein the cell culture is further provided with supplementary components.

5. The method of claim 4, wherein the supplementary components are provided in a feed medium.

6. The method of claim 4, wherein the supplementary components are selected from the group consisting of hormones, growth factors, sodium, chloride, calcium, magnesium, and phosphate ions, buffers, vitamins, nucleosides or nucleotides, trace elements, amino acids, lipids, glucose, and combinations thereof.

7. The method of claim 5, wherein the supplementary components include an anti-senescence compound, wherein the anti-senescence compound is selected from the group consisting of carnosine, acetyl-carnosine, homo-carnosine, anserine, and beta-alanine and combinations thereof.

8. A method for producing a TNFR fusion protein comprising steps of:
   culturing mammalian cells that contain a gene encoding the TNFR fusion protein in a cell culture medium, which gene is expressed under conditions of cell culture, at a first temperature or temperature range conducive for cell growth during a growth phase;
   shifting the temperature or temperature range of the cell culture medium to a second temperature or temperature range conducive for protein production;
   culturing the host cells in the cell culture medium at the second temperature or temperature range through a transition phase and into a production phase;
   wherein an anti-senescence compound is added to the cell culture, wherein the anti-senescence compound is selected from the group consisting of carnosine, acetyl-carnosine, homo-carnosine, anserine, and beta-alanine and combinations thereof; and
   harvesting the cell culture medium, which contains the protein;
   wherein the mammalian cells are Chinese hamster ovary (CHO) cells.

9. The method of claim 8, wherein the anti-senescence compound comprises carnosine.

10. The method of claim 8, wherein the anti-senescence compound is present in the cell culture medium at a concentration of between about 5 mM and about 100 mM.

11. The method of claim 8, wherein the cell culture is further provided with supplementary components.

12. The method of claim 11, wherein the supplementary components are provided in a feed medium.

13. The method of claim 11, wherein the supplementary components are selected from the group consisting of hormones, growth factors, sodium, chloride, calcium, magnesium, and phosphate ions, buffers, vitamins, nucleosides or nucleotides, trace elements, amino acids, lipids, glucose, and combinations thereof.

14. The method of claim 12, wherein the supplementary components include an anti-senescence compound selected from the group consisting of carnosine, acetyl-carnosine, homo-carnosine, anserine, and beta-alanine and combinations thereof, wherein the supplementary components include an anti-senescence compound.

15. The method of claim 1 or 8, wherein the produced TNFR fusion protein is heterologous to the CHO cells.

16. The method of claim 1 or 8, wherein the TNFR fusion protein comprises TNFR-Fc.

17. The method of claim 16, wherein the TNFR-Fc is etanercept.

18. A method for preparing a protein according to claim 1 or 8, further comprising the step of isolating the protein from the cell culture medium.

19. A method according to claim 18, wherein the protein is further purified or processed for formulation.

20. A method according to claim 19, wherein the protein is formulated into a pharmaceutical composition.

21. The method according to claim 1, further wherein the cell culture medium is shifted from a growth phase to a transition phase and a production phase, and wherein the anti-senescence compound is added to the cell culture medium during the transition phase, the production phase, or both the transition phase and production phase.

22. The method according to claim 8, further wherein the cell culture medium is shifted from a growth phase to a transition phase and a production phase, and wherein the anti-senescence compound is added to the cell culture medium during the transition phase, the production phase, or both the transition phase and production phase.

23. The method according to claim 3, wherein the anti-senescence compound is present in the cell culture medium at a concentration of about 20 mM.

24. The method according to claim 3, wherein the anti-senescence compound is present in the cell culture medium at a concentration of about 10 mM to about 40 mM.

25. A method of decreasing accumulation of high molecular weight aggregates during production of a TNFR fusion protein in cell culture comprising steps of:
   culturing Chinese hamster ovary (CHO) cells that contain a gene encoding the TNFR fusion protein, which gene is expressed under conditions of cell culture, in a cell culture medium comprising; and
   maintaining the culture under conditions and for a time sufficient to permit expression of the protein; and
   harvesting the cell culture medium, which contains the protein.

26. The method according to claim 25, wherein the carnosine is present in the cell culture medium at a concentration of about 10 mM to about 40 mM.

27. The method according to claim 26, wherein the carnosine is present in the cell culture medium at a concentration of about 20 mM.

28. A method of decreasing accumulation of acidic species during production of a TNFR fusion protein in cell culture comprising steps of:
   culturing Chinese hamster ovary (CHO) cells that contain a gene encoding the TNFR fusion protein, which gene is expressed under conditions of cell culture, in a cell culture medium comprising carnosine; and maintaining the culture under conditions and for a time sufficient to permit expression of the protein.

29. The method according to claim 28, wherein the carnosine is present in the cell culture medium at a concentration of about 10 mM to about 40 mM.

30. The method according to claim 29, wherein the carnosine is present in the cell culture medium at a concentration of about 20 mM.

\* \* \* \* \*

UNITED STATES PATENT AND TRADEMARK OFFICE
CERTIFICATE OF CORRECTION

| | | |
|---|---|---|
| PATENT NO. | : 12,054,762 B2 | Page 1 of 1 |
| APPLICATION NO. | : 12/107533 | |
| DATED | : August 6, 2024 | |
| INVENTOR(S) | : Jose Manuel Gomes et al. | |

It is certified that error appears in the above-identified patent and that said Letters Patent is hereby corrected as shown below:

In the Claims

Claim 25, Column 26, Line 52, insert after comprising --carnosine--

Signed and Sealed this
First Day of October, 2024

*Katherine Kelly Vidal*

Katherine Kelly Vidal
*Director of the United States Patent and Trademark Office*